(12) United States Patent
Lachaine et al.

(10) Patent No.: US 8,000,442 B2
(45) Date of Patent: Aug. 16, 2011

(54) CALIBRATING IMAGING DEVICES

(75) Inventors: Martin Lachaine, Montréal (CA); Tony Falco, La Prairie (CA); Véronique Audet, Montréal (CA); Xing Huang, Montréal (CA)

(73) Assignee: Resonant Medical, Inc., Montreal (CA)

( * ) Notice: Subject to any disclaimer, the term of this patent is extended or adjusted under 35 U.S.C. 154(b) by 1254 days.

(21) Appl. No.: 11/184,745

(22) Filed: Jul. 19, 2005

(65) Prior Publication Data

US 2006/0036170 A1 Feb. 16, 2006

Related U.S. Application Data

(60) Provisional application No. 60/589,432, filed on Jul. 20, 2004, provisional application No. 60/590,823, filed on Jul. 23, 2004.

(51) Int. Cl.
*A61N 5/10* (2006.01)
(52) U.S. Cl. .......... 378/65; 600/407; 600/437; 600/449; 382/154
(58) Field of Classification Search .......... 600/407–409, 600/437–472; 128/653.1, 653.2, 653.5, 916; 73/1.75, 1.79, 1.82, 1.86; 378/65, 162, 163, 378/98.5; 606/130; 364/413.01, 413.22
See application file for complete search history.

(56) References Cited

U.S. PATENT DOCUMENTS

| | | | |
|---|---|---|---|
| 3,082,322 A | 3/1963 | Koerner et al. | 250/61.5 |
| 3,777,124 A | 12/1973 | Pavkovich | 235/151 |
| 3,987,281 A | 10/1976 | Hodes | 235/151.3 |
| 3,991,310 A | 11/1976 | Morrison | 250/312 |
| 4,118,631 A | 10/1978 | Froggatt | 378/65 |
| 4,618,978 A | 10/1986 | Cosman | 378/164 |
| 4,923,459 A | 5/1990 | Nambu | 606/130 |
| 4,943,990 A | 7/1990 | Schär | 378/152 |
| 5,039,867 A | 8/1991 | Nishihara et al. | 250/492.3 |
| 5,080,100 A | 1/1992 | Trotel | 128/653.1 |
| 5,099,846 A | 3/1992 | Hardy | 128/653.1 |
| 5,107,839 A | 4/1992 | Houdek et al. | 128/653.1 |
| 5,117,829 A | 6/1992 | Miller et al. | 128/653.1 |
| 5,207,223 A | 5/1993 | Adler | 128/653.1 |
| 5,222,499 A | 6/1993 | Allen et al. | 128/653.1 |
| 5,291,889 A | 3/1994 | Kenet et al. | 128/653.1 |

(Continued)

FOREIGN PATENT DOCUMENTS

DE 2004003757 I1 11/2009

(Continued)

OTHER PUBLICATIONS

Besl et al., *A Method for Registration of 3d Shapes*, IEEE Transactions on Pattern Analysis and Machine Intelligence 14(2):239-256 (1992).

(Continued)

*Primary Examiner* — Tse Chen
*Assistant Examiner* — Baisakhi Roy
(74) *Attorney, Agent, or Firm* — Goodwin Procter LLP

(57) ABSTRACT

Methods and apparatus for calibrating images and imaging devices to common coordinate systems utilize, in some embodiments, rods that detectably reflect an acoustic signal regardless of the incidence angle of the signal with respect to the rods. Typically, the rods are disposed within a "phantom" at known positions with respect to a room coordinate system. Images of the cylindrical rods may be obtained from different directions, allowing the imaging device to be calibrated to the room coordinate system.

46 Claims, 12 Drawing Sheets

U.S. PATENT DOCUMENTS

| | | | |
|---|---|---|---|
| 5,295,483 A | 3/1994 | Nowacki et al. | 128/660.03 |
| 5,301,674 A | 4/1994 | Erikson et al. | 128/661.01 |
| 5,379,642 A | 1/1995 | Reckwerdt et al. | 73/625 |
| 5,391,139 A | 2/1995 | Edmundson | 600/7 |
| 5,411,026 A | 5/1995 | Carol | 128/660.03 |
| 5,442,675 A | 8/1995 | Swerdloff et al. | 378/65 |
| 5,447,154 A | 9/1995 | Cinquin et al. | 128/653.1 |
| 5,511,549 A | 4/1996 | Legg et al. | 128/653.1 |
| 5,531,227 A | 7/1996 | Schneider | 128/653.1 |
| 5,531,520 A | 7/1996 | Grimson et al. | |
| 5,609,485 A | 3/1997 | Bergman et al. | 434/262 |
| 5,673,300 A | 9/1997 | Reckwerdt et al. | 378/65 |
| 5,690,108 A | 11/1997 | Chakeres | 128/653.1 |
| 5,715,166 A | 2/1998 | Besl et al. | 364/4.24 |
| 5,754,623 A | 5/1998 | Seki | 378/65 |
| 5,810,007 A | 9/1998 | Holupka et al. | 600/439 |
| 5,871,445 A * | 2/1999 | Bucholz | 600/407 |
| 5,991,703 A | 11/1999 | Kase | 702/167 |
| 6,019,724 A | 2/2000 | Gronningsaeter et al. | 600/439 |
| 6,106,470 A | 8/2000 | Geiser et al. | 600/443 |
| 6,117,081 A | 9/2000 | Jago et al. | 600/443 |
| 6,118,848 A * | 9/2000 | Reiffel | 378/65 |
| 6,122,341 A | 9/2000 | Butler et al. | 378/20 |
| 6,129,670 A | 10/2000 | Burdette et al. | 600/427 |
| 6,138,495 A * | 10/2000 | Paltieli et al. | 73/1.86 |
| 6,285,805 B1 | 9/2001 | Gueziec | 382/299 |
| 6,292,578 B1 | 9/2001 | Kalvin | 382/131 |
| 6,345,114 B1 | 2/2002 | Mackie et al. | 382/132 |
| 6,359,959 B1 | 3/2002 | Butler et al. | 378/20 |
| 6,385,286 B1 | 5/2002 | Fitchard et al. | 378/65 |
| 6,390,982 B1 | 5/2002 | Bova et al. | 600/443 |
| 6,438,202 B1 | 8/2002 | Olivera et al. | 378/65 |
| 6,516,046 B1 | 2/2003 | Frohlich et al. | 378/65 |
| 6,535,574 B1 | 3/2003 | Collins et al. | 378/65 |
| 6,546,073 B1 | 4/2003 | Lee | 378/65 |
| 6,553,152 B1 | 4/2003 | Miller et al. | 382/294 |
| 6,560,311 B1 | 5/2003 | Shepard et al. | 378/65 |
| 6,585,651 B2 * | 7/2003 | Nolte et al. | 600/449 |
| 6,591,127 B1 | 7/2003 | McKinnon | 600/411 |
| 6,628,983 B1 | 9/2003 | Gagnon | 600/431 |
| 6,636,622 B2 | 10/2003 | Mackie et al. | 382/132 |
| 6,661,870 B2 | 12/2003 | Kapatoes et al. | 378/65 |
| 6,683,985 B1 | 1/2004 | Kase et al. | 382/203 |
| 6,915,008 B2 * | 7/2005 | Barman et al. | 382/154 |
| 2001/0035871 A1 | 11/2001 | Bieger et al. | 345/630 |
| 2002/0018588 A1 | 2/2002 | Kusch | 382/131 |
| 2002/0082494 A1 | 6/2002 | Balloni et al. | 600/410 |
| 2002/0156375 A1 | 10/2002 | Kessman et al. | 600/439 |
| 2002/0176541 A1 | 11/2002 | Schubert et al. | 378/65 |
| 2002/0183610 A1 | 12/2002 | Foley et al. | 600/407 |
| 2002/0188194 A1 | 12/2002 | Cosman | 600/426 |
| 2003/0018232 A1 | 1/2003 | Elliott et al. | 600/1 |
| 2003/0112922 A1 | 6/2003 | Burdette et al. | 378/65 |

FOREIGN PATENT DOCUMENTS

| | | |
|---|---|---|
| EP | 0 647 457 | 4/1995 |
| EP | 1 304 960 | 6/2005 |
| WO | 99/06644 | 4/1992 |
| WO | 99/26534 | 6/1999 |
| WO | 99/27839 | 6/1999 |
| WO | 03/076003 A2 | 9/2003 |
| WO | 03/076003 A3 | 9/2003 |

OTHER PUBLICATIONS

Booth, *Modelling the impact of treatment uncertainties in radiotherapy*, University of Adelaide, Mar. 2002), Section 2.4 (http://thesis.library.adelaide.edu.au/uploads/approved/adt-SUA20020816.175301/public/03chapter2.pdf.

Brujic et al., *Analysis of Free-Form Surface Registration*, International Conference on Image Processing, pp. 393-396 (1996).

Cuisenaire, O., http://www.tele.ucl.ac.be/PEOPLE/OC/these/node74.html, Posted Oct. 5, 1999, Downloaded from the Internet on Aug. 10, 2004.

Cuisenaire, O., http://www.tele.ucl.ac.be/PEOPLE/OC/these/node75.html, Posted Oct. 5, 1999, Downloaded from the Internet on Aug. 10, 2004.

Cuisenaire, O., http://www.tele.ucl.ac.be/PEOPLE/OC/these/node12.html, Posted Oct. 5, 1999, Downloaded from the Internet on Aug. 10, 2004.

Dubois et al. *Intraobserver and Interobserver Variability of MR Imaging- and CT-derived Prostate Volumes after Transperineal Interstitial Permanent Prostate Brachytherapy*, Radiology. 207(3):785-9 (1998).

Eggert et al., *Simultaneous Registration of Multiple Range Views for Reverse Engineering*, International Conference of Pattern Recognition, pp. 243-247 (1996).

Hanks, et al., *Three Dimensional Conformal External Beam Treatment of Prostate Cancer* http://prostate-help.org/download/pilgrim/10rad.pdf.

Hanks et al., *Clinical and Biochemical Evidence of Control of Prostate Cancer at 5 Years After External Beam Radiation*, The Journal of Urology, vol. 154, 456-459 (1995).

Haralick et al., *Pose Estimation From Corresponding Data Point*, IEEE Transactions on Systems, Man, and Cybernetics, 19(6):1426-1446 (1989).

Hua et al., *Development of a Semi-Automatic Alignment Tool for Accelerated Localization of the Prostate*, Int. J. Radiation Oncology Biol. Phys., 55(3):811-823 (2003).

Jiang et al., *A New Approach to 3-d Registration of Multimodality Medical Images by Surface Matching*, SPIE vol. 1808 Visualization in Biomedical Computing, pp. 196-213 (1992).

Krempien et al., *Daily patient set-up control in radiation therapy by coded light projection*, 3 pages.

Michalski et al., *Three-Dimensional Conformal Radiation Therapy (3DCRT) for Prostate Cancer*, Radiation Oncology Center, Mallinckrodt Institute of Radiology, Washington University Medical Center, St. Louis, Missouri (1996) http://www.phoenix5.ore/Infolink/Michalski/#3.

Paskalev et al., *Daily Target Localization for Prostate Patients based on 3-D Image Correlation*, Phys. Med. Biol., vol. 49, pp. 931-939 (2004).

Pennec et al,. *A Framework for Uncertainty and Validation of 3-D Registration Methods Based on Points and Frames*, International Journal of Computer Vision 25(3), 203-229 (1997).

Pito, *A Registration Aid*, International Conference on Recent Advanced in 3D Digital Imaging and Modelling, pp. 85-92 (1997).

Pollack et al., *Conventional vs. Conformal Radiotherapy for Prostate Cancer: Preliminary Results of Dosimetry and Acute Toxicity*, Int. J. Radiation Oncology Biol. Phys., 34(3):555-564.

Robb, *Three-Dimensional Visualization in Medicine and Biology*. Book Chapter in: Handbook of Medical Imaging: Processing and Analysis, ed. Isaac N. Bankman, Academic Press, San Diego, CA, Chapter 42, pp. 685-771 (2000).

Robinson, *Advances in Multi-Modal Data Analysis: The ANALYZE Software Environment*, http://www.ii.metu.edu.tr/~med-ii/makaleler/analyze_sw_enve.pdf, 5 pages. Downloaded on Aug. 10, 2004.

Soffen E.M. et al. *Conformal static field radiation therapy treatment of early prostate cancer versus non-conformal techniques: A reduction in acute morbidity*. Int J Radiat Oncol Biol Phys, 24: 485-488 (1992).

Thayananthan, A. et al., http://mi.eng.cam.ac.uk/~bdrs2/papers/thayananthan_cvpr03.pdf, pp. 1-8. Downloaded from the Internet on Aug. 10, 2004.

Tome et al., *Commissioning and Quality Assurance of an Optically Guided Three-dimensional Ultrasound Target Localization System for Radiotherapy*, Med. Phys., 29(8):1781-1788 (2002).

Zhang, *Iterative Point Matching for Registration of Free-Form Curves and Surfaces*, International Journal of Computer Vision, 13(2):119-152 (1994).

http://www.ucsf.edu/jpouliot/Course/chapter5.htm.
http://www.acmp.org/meetings/hershey_2001/highlights/benedict.pdf.
http://www.ucsf.edu/ipouliot/Course/Lesson22.htm.
http://www.gemedicalsystems.com/patient/see_treat/positioning.html.
http://www.emoryradiationoncology.org/high-technology.htm.
http://www.varian.com/pinf/imr000c.html.

http://www.ucsf.edu/jpouliot/Course/conformal_radiation_therapy.htm.

Boctor, et al., *A Rapid Calibration Method for Registration and 3D Tracking of Ultrasound Images Using Spatial Localizer*, Proceedings of the SPIE (2003).

Claim Chart for Claim 10 of US Patent No. 5,447,154.

Van de Geijn, J. et al. *A Graticule for Evaluation of Megavolt X Ray Port Films*, Radiation Oncology Biology Physics, Nov. 1982, vol. 8, No. 11 pp. 1999-2000.

Bijhold, J. et al. *Fast evaluation of patient set-up during radiotherapy by aligning features in portal and simulator images*, Phys. Med. Biol., 1999, vol. 36, No. 12, pp. 1665-1679.

Meertens, H. et al. *A method for the measurement of field placement errors in digital portal images*, Phys. Med. Biol., 1990, vol. 35, No. 3, pp. 299-323.

Aoki, Y. et al. *An Integrated Radiotherapy Treatment System and its Clinical Application*, Radiation Medicine, vol. 5, No. 4, pp. 131-141, 1987.

Troccaz, J. et al. *Conformal external radiotherapy of prostatic carcinoma: requirements and experimental results*, Radiotherapy and Oncology 29 (1993) pp. 176-183.

Le Verre, C. et al. *Intensity-Based Registration of Portal Images for Patient Positioning in Radiotherapy*.

Brunie L. et al. *Pre-and intra-irradiation multimodal image registration: principles and first experiments*, Radiotherapy and Oncology 29 (1993) pp. 244-252.

Troccaz., J et al. *Patient Setup Optimization for External Conformal Radiotherapy*, Journal of Image Guided Surgery, 1, pp. 113-120 (1995).

Simpson, R.G. et al. *A 4-MV CT scanner for radiation therapy: The prototype system*. Med. Phys. 9(4), Jul./Aug. 1982, pp. 574-579.

Swindell, W. et al. *Computed tomography with a linear accelerator with radiotheraphy applications*, Med. Phys. 10(4), Jul./Aug. 1983, pp. 416-420.

Reinstein, L. et al. *Radiotherapy Portal Imaging Quality, Report of AAPM Task Group No. 28*, American Association of Physicists in Medicine by the American Institute of Physics, New York, 1988.

Bijhold, J. *Three-dimensional verification of patient placement during radiotherapy using portal images*, Med. Phys. 20 (2), Pt. 1, Mar./Apr. 1993. pp. 347-356.

Boyer, A. *A review of electronic portal imaging devices (EPIDs)*, Med. Phys. 19 (1), Jan./Feb. 1992 pp. 1.

International Search Report for PCT/CA2005/001428 dated Nov. 16, 2005.

Written Opinion of the International Searching Authority dated Nov. 8, 2005.

Czarnota G.J. et al. *Ultrasound imaging of apoptosis: high-resolution non-invasive monitoring of programmed cell death in vitro, in situ and in vivo*, British Journal of Cancer (1999) 81(3), pp. 520-527.

Supplementary European Search Report, for PCT Application No. PCT/CA2005001135, dated Feb. 27, 2009 (12 pages).

Barratt, Dean C., "Accuracy of an Electromagnetic Three-Dimensional Ultrasound System for Carotid Artery Imaging" from Ultrasound in Medicine and Biology, vol. 27, No. 10, 2001, pp. 1421-1425.

\* cited by examiner

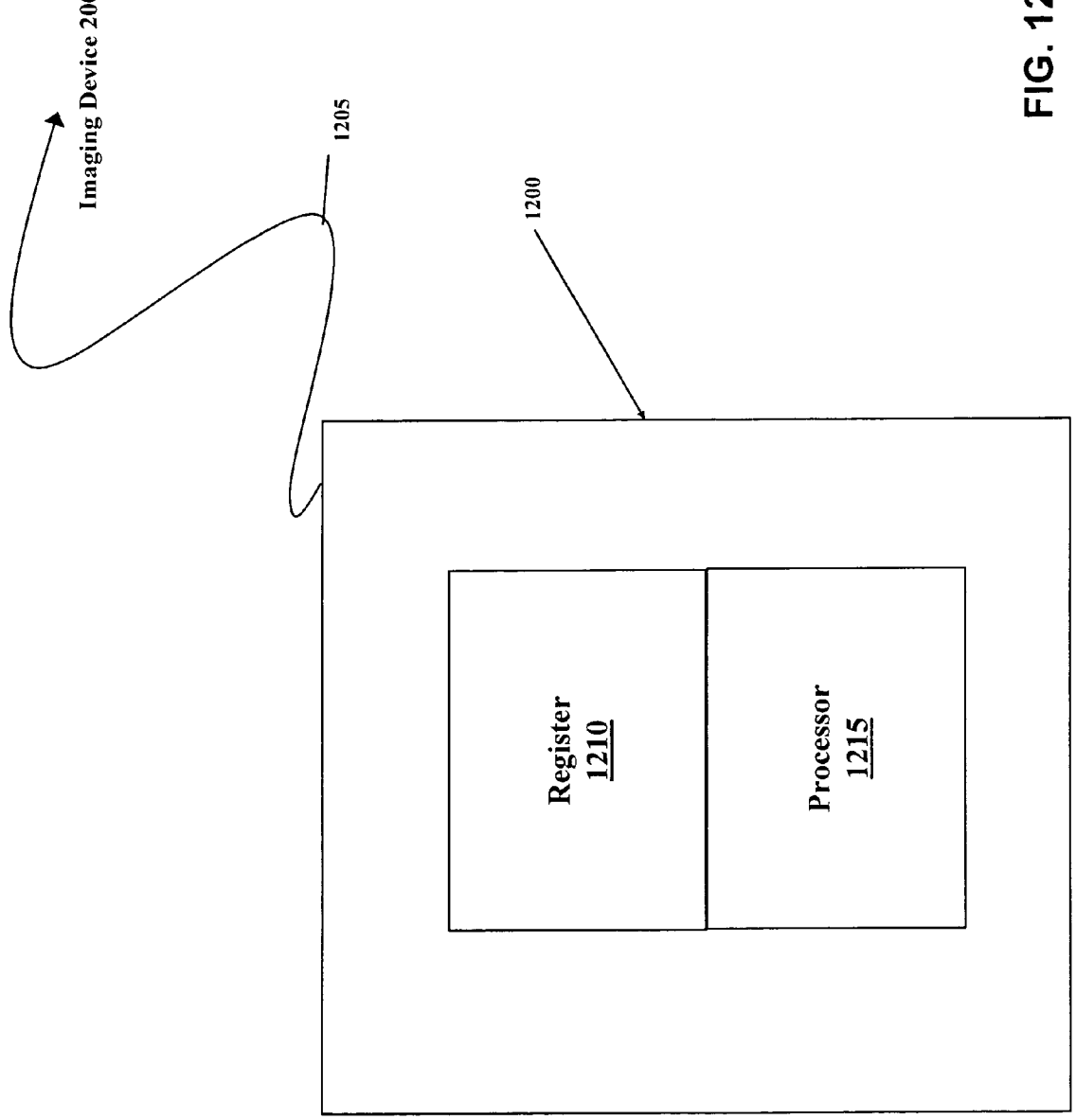

CALIBRATING IMAGING DEVICES

CROSS-REFERENCE TO RELATED APPLICATIONS

This application claims priority to U.S. provisional patent application Ser. No. 60/589,432, filed Jul. 20, 2004, and U.S. provisional patent application Ser. No. 60/590,823, filed Jul. 23, 2004.

FIELD OF THE INVENTION

The invention relates generally to the field of medical imaging, and, in particular, to calibrating medical imaging devices to reference coordinate systems.

BACKGROUND INFORMATION

Hand-held two-dimensional ultrasound devices are used to create diagnostic images of anatomical features of a patient. Because many of the images are further used to plan and administer treatment to organs, lesions, and other anatomical structures, the accuracy of the images is critical. One aspect of an image's accuracy is the degree to which the structures in the image can be placed at identifiable locations in space relative to a set of fixed markers or a known reference coordinate system.

One approach is to calibrate the ultrasound device using a structure with embedded elements placed at known positions in a coordinate system and using images of the structure and the known locations of the elements within it to calibrate the imaging device. The device may then be registered, for example, to another imaging device coordinate system, treatment unit coordinate system, or room reference coordinate system.

Traditionally, such structures (known as "phantoms") contain a series of wires in a known arrangement to each other (e.g., all parallel, orthogonal, etc.). However, wires can only be detected with ultrasound from very specific angles, making it difficult to acquire sufficient independent images to use for calibration. Using such phantoms requires multiple images taken from multiple sides of the phantom and at very specific angles in order to detect the wires. This increases the complexity and amount of time needed to perform the calibration, and introduces potential sources of error.

What is needed, therefore, are methods, systems, and apparatus that facilitate the convenient, rapid and accurate calibration of ultrasound images to a hand-held ultrasound device, and registration of the device to a fixed coordinate system.

SUMMARY OF THE INVENTION

The present invention provides methods, apparatus and systems that facilitate a more rapid and simplified calibration process for imaging devices. More specifically, the process for calibrating hand-held ultrasound probes to a coordinate system of other imaging and/or treatment devices within a room is greatly simplified through improved calibration tools and the application of mathematical transforms to relate otherwise independent reference systems to each other. Using the methods and apparatus described below, technicians can quickly calibrate an imaging device using images from virtually any angle with respect to a calibration device, and because fewer images are required compared to previous calibration processes, the time needed to perform the calibration process is reduced. In some embodiments, the invention pertains to a calibration tool utilizing imageable components that have diffuse reflection characteristics, thereby alleviating the specific incidence angle constraints that exist with respect to wire-based calibration devices. Some embodiments of the invention pertain to the ability to track the device in three-dimensional space, without regard to the location of the device in the room, providing additional flexibility with respect to device positioning during calibration.

In accordance with the present invention, an ultrasound phantom containing a series of elongated members (such as cylindrical rods) is used to accurately register images taken by a hand-held ultrasound probe to known reference coordinate systems. The geometry of the elongated members is such that they reflect ultrasound waves diffusely, rather than specularly. As a result, two-dimensional ultrasound images taken using the probe can be accurately related to the coordinate system of the imaging device, and in turn, to the three-dimensional room coordinate system, thus providing valuable diagnostic and treatment data such as the location and shape of a tumor, organ, lesion, or other anatomical structure or structures.

In one aspect, the present invention provides methods for calibrating an imaging device to a reference coordinate system. A plurality of elongated members (e.g., cylindrical rods) that detectably reflect acoustic signals regardless of a signal's angle of incidence with respect to the members are placed at known positions with respect to a reference coordinate system. A plurality of images (e.g., two-dimensional ultrasound images) are taken from different directions with respect to the members using an imaging device, each image including representations of the members. The imaging device is then calibrated to the reference coordinate system based on the images of the members.

The reference coordinate system may be, for example, a three-dimensional reference coordinate system that, in some embodiments, is defined by a series of lasers disposed about a room and/or the physical orientation of a treatment device such as a LINAC or an imaging device such as a CT scanner or MRI. The two-dimensional ultrasound images can be taken from different angles with respect to the members, including, for example, orthogonal to or oblique to the members. In some embodiments the calibration step includes determining the centers of one or more of the members within the representations, and may also include determining the coordinates of the members with respect to the reference coordinate system based on the determined centers. The calibration of the imaging device may further include relating the images to a coordinate system of the imaging device, and relating the coordinate system of the device to the reference coordinate system. The elongated member can be of any shape so long as cross-sectional images taken at various angles through the member are concentric, and this condition will be fulfilled for most straight, rod-like members. Preferred elongated members have shapes that do not vary across their lengths (i.e., have consistent cross-sections, regardless of whether the cross-section is round, elliptical, square, triangular, many-sided, etc.). In some embodiments, the imaging device is recalibrated to the reference coordinate system in response to a second set of images taken at an image depth different from that of the received plurality of images.

In another aspect, a system for calibrating an imaging device to a reference coordinate system includes a register for receiving images (e.g., two-dimensional ultrasound images) taken from a number of different locations, where the images include representations of elongated members (such as cylindrical rods) that have known positions with respect to a reference coordinate system and that detectably reflect acoustic signals regardless of the angle of incidence of the signal with respect to the members. The system also includes a processor for calibrating the imaging device to the reference coordinate system based on the images.

In some embodiments, the processor further determines the centers of one or more of the members within the representations, and in some cases relates these determined centers to the coordinates of the reference coordinate system. The reference coordinate system may be a three-dimensional reference coordinate system defined, for example, by a series of lasers disposed about the room and/or the physical orientation of a treatment device such as a LINAC or an imaging device such as a CT scanner or MRI. The processor, in some embodiments, recalibrates the imaging device to the reference coordinate system in response to a second set of images taken at an image depth different from that of the received plurality of images.

In a third aspect, an apparatus for calibrating an imaging device to a reference coordinate system includes a first housing with elongated members placed at fixed positions inside the first housing and at known positions with respect to a reference coordinate system, and a second housing on the first housing that includes target areas placed about the second housing for placement of an imaging device. When placed at the targets, the imaging device produces images that include representations of the members in the first housing.

The elongated members should be of sufficient size such that they detectably reflect an acoustic signal regardless of incidence angle of the signal with respect to the members. The shape of the elongated members may be any shape such that cross-sectional images of a particular member are concentric regardless of sectional angle. The elongated members may be rods, and in some preferred embodiments, cylindrical rods. The minimum diameter necessary for adequate reflection characteristics depends on the wavelength of the acoustic signal. In general, good results have been obtained using standard ultrasound equipment with rods having a diameter of approximately 12 mm.

In some embodiments, the target areas are apertures. The apertures may be sized, or located within a slot or shaped recess, such that an imaging device is received in close-fitting relation, and in some embodiments, the imaging device is repositionable in more that one orientation within the apertures or recesses. The repositioning may be indexible. In some cases, the imaging device is rotatable about an axis, the axis in some embodiments passing through the imaging device, whereas in other embodiments the axis of rotation is external to the device. In some embodiments, support arms (e.g., for holding the imaging device) may be mated (either permanently or temporarily) to the second housing, by, for example, inserting them into openings in the second housing. The first and second housings may, in some cases, be integral.

In another aspect, the invention provides a method for calibrating an imaging device (e.g., an ultrasound probe) to a reference coordinate system. The method includes locating, at known positions with respect to a reference coordinate system, objects that diffusely reflect an acoustic signal from an imaging device, applying an acoustic signal to the objects to obtain images based on the diffuse reflection of the signal and calibrating the imaging device to the reference coordinate system based on the images.

The reference coordinate system can be a three-dimensional reference coordinate system defined, for example, by a series of lasers disposed about the room and/or the physical orientation of a treatment device such as a LINAC or an imaging device such as a CT scanner or MRI.

In another aspect, the invention provides an apparatus for obtaining ultrasonic images. The apparatus includes a hand-held probe with an elongated handle, and a faceplate (which may be curved or composed of multiple flat plates) disposed circumferentially about the handle and partially surrounding the handle. Multiple signal emitters (e.g., infrared) or reflectors are located at various locations about the faceplate.

In some embodiments, the probe houses an ultrasound imaging device. In some embodiments, the infrared emitters are in communication with a device for positioning, and can therefore take multiple ultrasonic images from numerous positions about a patient while remaining within infrared "sight" of the tracking device.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

FIG. 12 is a schematic illustration of an imaging calibration system according to an embodiment of the invention.

DETAILED DESCRIPTION

Figure 1:
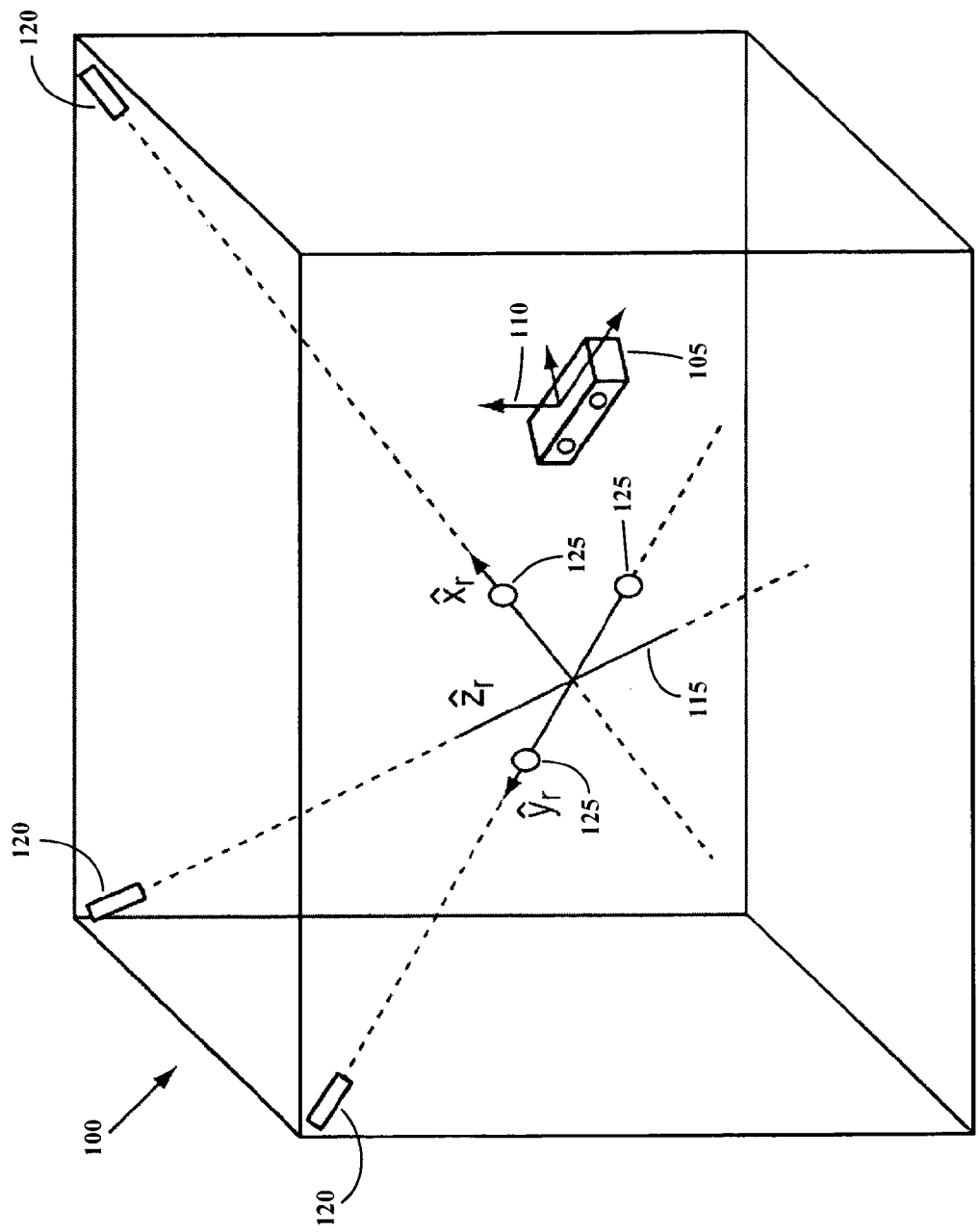
FIG. 1 is a graphical representation of a room coordinate system calibration system according to an embodiment of the invention.

Throughout the following descriptions and example, the illustrative descriptions of the invention is described in the context of calibrating a hand-held ultrasound imaging probe to a three-dimensional reference coordinate system defined in a radiation treatment room. However, it is to be understood that the present invention may be applied to calibrating the location of virtually any hand-held imaging device to any reference coordinate system.

Radiation-emitting devices are used for the treatment of cancerous tumors within patients. The primary goal of radiation therapy is the complete eradication of the cancerous cells, while the secondary goal is to avoid, to the maximum possible extent, damaging healthy tissue and organs in the vicinity of the tumor. Typically, a radiation therapy device includes a particle linear accelerator ("LINAC") that generates a high-energy radiation beam of therapy, such as an electron beam or photon (x-ray) beam. The patient is placed on a treatment table located at the isocenter of the gantry, and the radiation beam is directed towards the tumor or lesion to be treated.

Radiation therapy typically involves a simulation/planning stage and a treatment stage. Generally, the simulation stage involves acquiring images of a lesion using, for example computed tomography (CT) or magnetic resonance imaging (MRI) and subsequently using these simulation image(s) to accurately measure the location, size, contour, and number of lesions to be treated. The images are used to establish certain treatment plan parameters, such as an isocenter, beam angles, energy, aperture, dose distribution, and other parameters in an attempt to irradiate the lesion while minimizing damage to surrounding healthy tissue.

Determining the treatment parameters in the planning stage generally requires anatomical information such as the location of the tumor and surrounding critical organs. These, too, are imaged, and a physician outlines the organs and volumes of interest, either manually or programmatically using one or more computer algorithms. The treatment plan is then designed to deliver the maximum radiation dose to the outlined target volume while minimizing the dose to surrounding healthy organs and normal tissue. The treatment plan can be designed manually by the user or by optimization algorithms.

Radiation treatments, dictated by a previously defined treatment plan, are typically delivered over a number of treatment sessions, for example one treatment each weekday for a total of 35 sessions. To ensure the accurate administration of each treatment, the technician attempts to position the patient the same way he was positioned during the acquisition of the images taken during treatment planning. Due to the sequential nature of these treatments, an uncertainty is introduced during the positioning of the patient at each successive treatment. Furthermore, internal organs may move between and/or during treatment sessions such that their shape and location differ from their initial state at the time of planning. These factors may compromise the accuracy and effectiveness of treatment.

In some embodiments of the present invention, the accuracy of the treatment plan is enhanced by co-locating a hand-held imaging device (an ultrasound scanner, for example) and a simulation imager (e.g., a CT or MRI device) used to capture images used during the treatment planning phase. In other embodiments, the accuracy of the delivered treatment may be enhanced by co-locating the hand-held imaging device and the LINAC in the same room. Because ultrasound imaging devices are generally hand-held and not fixed in space, calibrating the images taken from such a device to the coordinate system of the room in which it is being used, and ultimately the simulation imager or LINAC, has proven difficult.

The methods and apparatus described below overcome these challenges and provide an easier, more accurate calibration of the imaging device, and thus facilitate an accurate calibration of the images taken using the device to a reference (e.g., planning or treatment room) coordinate system.

The relationship between a coordinate system of a tracker device that is fixed in space within a treatment and/or imaging room and a coordinate system of that room is determined and expressed as a tracker-to-room transformation. In addition, an apparatus (referred to herein as a "phantom") containing rods that are visible to an ultrasound scanner is placed in the room at a known location with respect to the room coordinate system such that the location of the rods are known with respect to the room coordinate system. An imaging device (e.g., a hand-held, two-dimensional ultrasound scanner) is placed on, in and/or near the phantom and multiple images are taken so they contain representations of the rods within the phantom, and the pixels within the images may be assigned to a known position with respect to the imaging device (the "frame-to-device" transformation). The center-point of the representations of the rods within the images is calculated to determine an accurate point of reference for the image with respect to the phantom. During the imaging process, the imaging device is tracked by the tracker, thereby providing a device-to-tracker transformation for each location of the imager in the tracker coordinate system. Pixels in each image frame generated by the device are related to the imager itself (i.e., to the device coordinate system) using the frame-to-device transformation. The device-to-tracker transformation is then used to associate the pixel data with the tracker coordinate system, and subsequently into the room coordinate system using the tracker-to-room transformation. Thus, specific pixel locations within multiple images taken using a hand-held, non-stationary device at various angles can be assigned coordinates in the three-dimensional room coordinate system, which may be used to guide the LINAC and/or register ultrasound images to simulation CT or MRI images.

Tracker-to-Room Transformation

Referring to FIG. 1, an imaging system in accordance with an embodiment of the invention is used to obtain images of a subject placed in a treatment or simulation room 100. In one embodiment, a tracker 105 is affixed anywhere in the room (e.g., on the ceiling, a wall, etc.). The tracker 105 tracks the position of at least one marker, and/or the position and rotation of a set of at least three markers, using a tracker coordinate system 110. One example of tracker 105 is an optical tracking device, which tracks active infrared emitting devices or passive optical reflectors. The room 100 may have a room coordinate system 115 which may or may not be aligned with the tracker coordinate system 110. The room coordinate system 115 may, in some cases, be related to the mechanical motion and/or placement of a radiation treatment device and/or simulation imager, and/or the patient support assembly (not shown). To aid in visualizing the room coordinate system 115, lasers 120 may be affixed within the room 100 and aligned such that they pass through the axes of the room coordinate system 115. To calibrate the tracker 105 to the room 100, an object, such as a phantom (described in more detail below), having markers 125 affixed to its structure in a known configuration is used to associate the room coordinate system 115 to the tracker coordinate system 110. The phantom is placed in a known position and orientation with respect to the room coordinate system 115, which may be represented by the room lasers 120. One or more images of the phantom and the affixed markers 125 are captured by the tracker 105. Knowledge of the position and orientation of the group of markers 125, relative to the room coordinate system, facilitates the tracker-to-room transformation. Markers may also be affixed to the imaging device, allowing the tracker to track the position and orientation of the imaging device and thereby enabling a device-to-tracker transformation.

Still referring to FIG. 1, room calibration may be accomplished by using, for example, three markers 125 affixed to a phantom tool (not shown) located at a known position in the room 100 (such as the phantom described herein) which can be tracked by the tracker 105. Thus, a coordinate system can be defined for this marker tool. A snapshot of the tool using the tracker 105 will facilitate the tracker-to-room transformation. For example, if the tracker 105 output is given by three translations ($t_x$, $t_y$, $t_z$) and four unit quaternion values ($q_o$, $q_x$, $q_y$, $q_z$), these can be converted to the tracker-to-room matrix by the operation $$^RT_T = \begin{pmatrix} R_{11} & R_{21} & R_{31} & -[R \cdot T]_1 \\ R_{21} & R_{22} & R_{32} & -[R \cdot T]_2 \\ R_{31} & R_{23} & R_{33} & -[R \cdot T]_3 \\ 0 & 0 & 0 & 1 \end{pmatrix} \quad (1)$$

where $$R = \begin{pmatrix} q_0^2 + q_x^2 - q_y^2 - q_z^2 & 2 \cdot (q_0 q_z + q_x q_y) & 2 \cdot (-q_0 q_y + q_x q_z) \\ 2 \cdot (-q_0 q_z + q_x q_y) & q_0^2 - q_x^2 + q_y^2 - q_z^2 & 2 \cdot (q_0 q_x + q_y q_z) \\ 2 \cdot (q_0 q_y + q_x q_z) & 2 \cdot (-q_0 q_x + q_y q_z) & q_0^2 - q_x^2 - q_y^2 + q_z^2 \end{pmatrix} \quad (2)$$

and $$T = \begin{pmatrix} t_x \\ t_y \\ t_z \end{pmatrix}. \quad (3)$$

Here $^RT_T$ is the tracker-to-room transformation, and R and T are its rotational and translational components respectively.

The markers 125 used for room calibration may or may not be affixed to the tool, but attaching them to the tool allows the same tool to be used for both the room and imaging device calibration processes. In one embodiment, external etchings on the tool casing allow the user to align the tool with the room lasers 120. In some cases, the markers 125 may be offset from the external etchings to facilitate alignment with lasers 120, in which case the shifts are accounted for in the definition of the room coordinate system. The offsets also help to keep the markers 125 in the field of view of the tracker 105 so that they are not obscured by the phantom. In some embodiments, the marker tool is asymmetric to ensure that the tracker and associated systems can uniquely detect rotations of the tool.

Relationship of Imaging Device to Tracker

To relate the images taken by a hand-held imaging device to a known coordinate system (e.g., the room coordinate system), a relationship between the pixels of the images generated by the imaging device and the coordinate system of the markers affixed to the imaging device is determined. This step is referred to herein as "probe calibration" and results in an image-to-device transformation that may be used to convert pixel coordinates from two-dimensional image space to the three-dimensional device coordinate system.

Figure 2B:
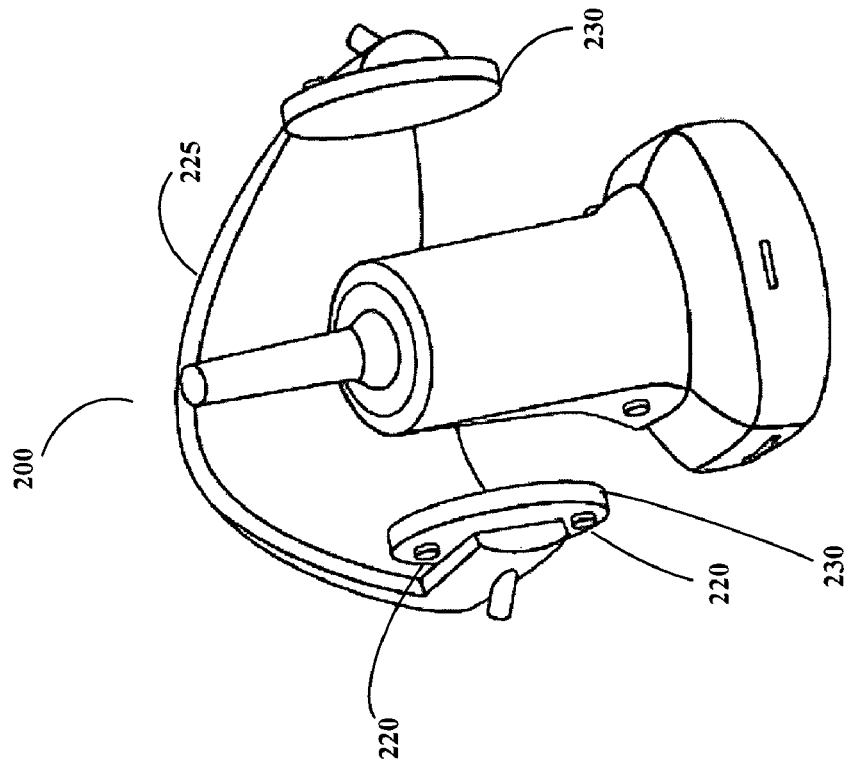
FIG. 2B is a perspective view of the hand-held imaging probe of FIG. 2A according to an embodiment of the invention.
Figure 2A:
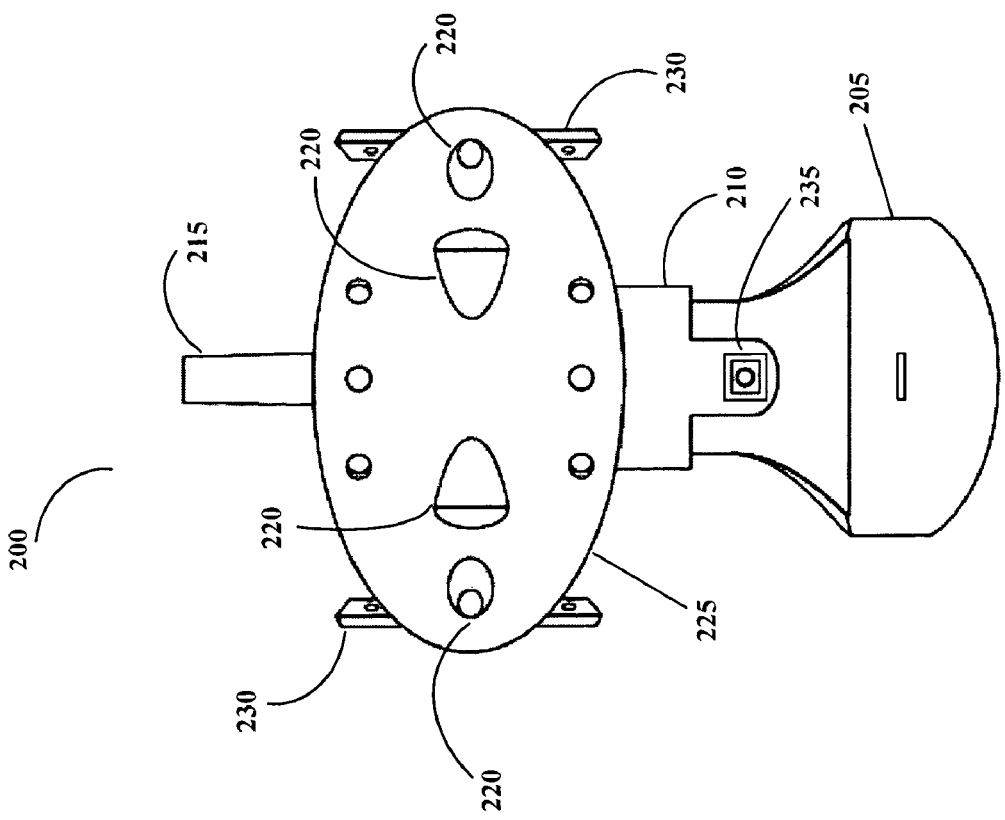
FIG. 2A is top view of a hand-held imaging probe according to an embodiment of the invention.

FIGS. 2A and 2B illustrate a hand-held imager 200 that may be tracked using the tracker device describe above in accordance with one embodiment of the invention. The probe 200 includes one or more imagers 205 for taking images from various angles using, for example, ultrasound. Although the imaging device portrayed in the figures and text herein is described as an ultrasound imager, other imaging modalities that utilize hand-held probes are also encompassed by the invention. One example of an imaging device includes, for example, the LUMAGEM Hand Held Gamma Camera by Gamma Medica, Inc. of Northbridge, Calif. The probe 200 also includes a handle 210 and a connection device 215 (e.g., a wire, cable, or other flexible or rigid connecter, or a wireless transceiver) that facilitates communication between the probe 200 and a central processing unit, computer or control unit (not shown). The probe 200 also includes one or more marker tools 220, such as infrared emitters, that may be tracked by the tracking device so that the position and the orientation of the probe 200 with respect to the tracking device is known during scanning. This allows the construction of three-dimensional datasets using the coordinates of the tracker coordinate system from two-dimensional ultrasound slices taken using the hand-held probe 200. In some embodiments, the probe 200 includes multiple (e.g., three) emitters to address cases when the probe 200 is not directly facing the tracker such as when a sagittal slice (i.e., a slice that is perpendicular to the transmit/receive faceplate of the tracking device) is being acquired. For example, in one embodiment the probe 200 includes a faceplate 225 and/or one or more sideplates 230 that surround the handle 210 (either partially or completely), each plate having one or more emitters 220 thereon. Emitters 200 are placed at various locations about the faceplate 225 and sideplates 230 of the probe 200 facing different directions, such that at least three emitters can be "seen" by the tracking device at any given time over a wide angle of probe directions. Although this configuration is preferred, different configurations can be used to achieve the same effect. A device coordinate system may then be defined relative to the markers affixed to the probe 200. The tracker records, either directly or indirectly, the device-to-tracker transformation for each position and orientation of the probe 200 for each image. This transformation changes as the probe is moved (e.g., when a patient is being scanned) and is stored for each probe position from which an image is taken, thus allowing each position of the probe 200 to be associated with a particular device-to-tracker transformation.

One or more buttons 235 that initiate and/or stop the scanning process are placed on the body of the probe 200 to facilitate scanning of a selected region of interest of the body.

Phantom

The device-to-tracker transformation determined by affixing markers to the probe 200 is not immediately related to the pixel values of the individual images generated by the probe 200. To relate the pixel values in the images to the device coordinate system, a frame-to-device transformation is determined. This is performed by using the device to obtain images of a calibration tool (i.e., a phantom) that includes embedded elements that appear in images taken using the device.

Figure 3:
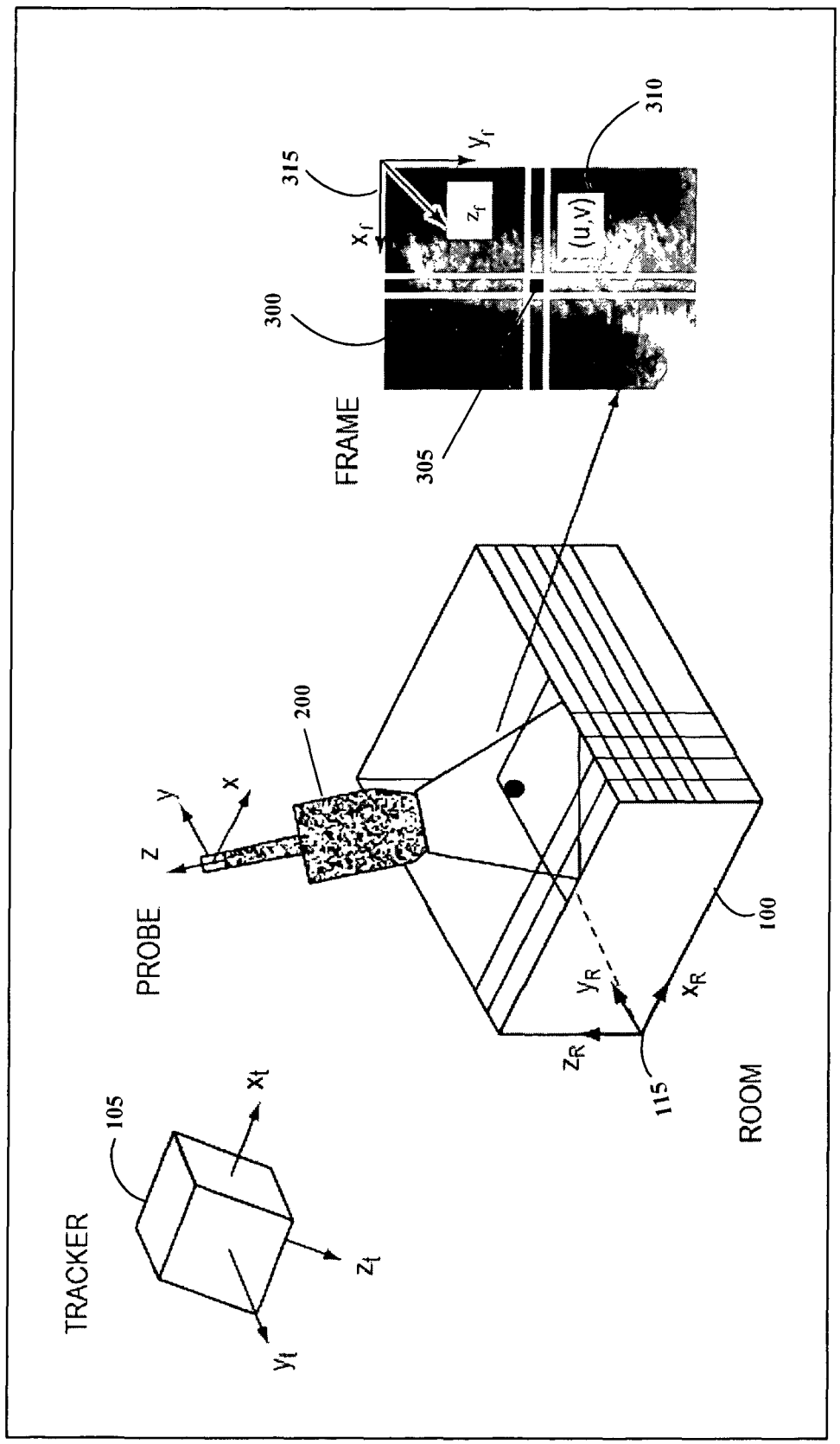
FIG. 3 is a graphical representation of an imaging system according to an embodiment of the invention.

With reference to FIG. 3, the probe 200 produces a series of images 300, or frames, as it is moved around in space. A frame or "slice" is defined as an image acquired with the imaging device at a given position and orientation. It can be acquired, for example, with the push of a button on the imaging device or by selection on a computer which controls the imaging device. As the number of slices increases, the calibration results improve, with a set of seven slices providing particularly good results. Each frame 300 has a series of pixels 305 which can be labeled by the indices (u,v) shown at 310. To use the frames 300 for planning purposes in conjunction with a treatment device, pixels 305 from one or more of the image frames 300 are associated with the room coordinate system 115 ($x_R, y_R, z_R$) in a series of steps, each using a mathematical transformation. The pixels 305 can be referenced using a frame coordinate system ($x_F, y_F, z_F$) indicated at 315, to allow each pixel 305 to have associated with it three-dimensional coordinates 315 within the frame coordinate system 315. The three-dimensional coordinates 315 may then be related to the device coordinate system (x,y,z) (which is arbitrarily defined with respect to the markers affixed to the probe 200) using the frame-to-device transformation described above. This device coordinate system may be related to the tracker coordinate system $(x_t, y_t, z_t)$ using the device-to-tracker transformation, which may be expressed in the room coordinate system $(x_R, y_R, z_R)$ by applying the tracker-to-room transformation. The device-to-tracker transformation is determined implicitly by the tracker 105 using the markers 125 as described above with reference to FIG. 1 and can be determined prior to or during the calibration processes. The tracker-to-room transformation and frame-to-device transformation are determined during the calibration process using the room calibration, method described above and the probe calibration method described below.

In accordance with one embodiment of the invention, the probe calibration process uses a phantom with embedded elements, as described below. However, the positions of the elements within the phantom must be known within the coordinate system of the phantom, i.e., the phantom coordinate system, so as to relate the locations of the embedded elements to the room coordinate system. One conventional method of determining the locations uses physical measurements of the elements with respect to the phantom casing.

Another method of locating the phantom with respect to the room coordinate system uses a phantom containing wires, which, when imaged using the device, appear as small dots on the ultrasound scans. The (u,v) positions of wires are identified under a series of two-dimensional ultrasound scans. Assuming the wires run along the x-direction in room coordinates $(y_R, z_R)$, positions of the wires are known relative to the external phantom casing. A set of equations can be defined relating (u,v) to the known positions in the room $(y_R, z_R)$:

$$\begin{pmatrix} x_R \\ y_R \\ z_R \\ 1 \end{pmatrix} = {}^R T_T \, {}^T T_D \, {}^D T_F \begin{pmatrix} u \\ v \\ 0 \\ 1 \end{pmatrix} \qquad (4)$$

where ${}^R T_T$, ${}^T T_D$, and ${}^D T_F$ are the tracker-to-room, device-to-tracker and frame-to-device transformations, respectively. Probe calibration refers to the determination of ${}^D T_F$, which includes two scaling parameters $s_x$ and $s_y$, three translational and three rotational parameters. These are the unknowns which must be solved for probe calibration.

In a particular coordinate system, each transformation matrix (except for the scaling part of ${}^D T_F$) can be expressed in terms of three rotation variables $(\alpha, \beta, \gamma)$ and three translation variables $(\Delta x, \Delta y, \Delta z)$ by $$T(\Delta x, \Delta y, \Delta z, \alpha, \beta, \gamma) = \begin{pmatrix} \cos\alpha\cos\beta & \cos\alpha\cos\beta\sin\gamma - \sin\alpha\cos\gamma & \cos\alpha\sin\beta\cos\gamma + \sin\alpha\sin\gamma & \Delta x \\ \sin\alpha\cos\beta & \sin\alpha\sin\beta\sin\gamma + \cos\alpha\cos\gamma & \sin\alpha\sin\beta\cos\gamma - \cos\alpha\sin\gamma & \Delta y \\ -\sin\beta & \cos\beta\sin\gamma & \cos\beta\cos\gamma & \Delta z \\ 0 & 0 & 0 & 1 \end{pmatrix} \qquad (5)$$

A set of three independent nonlinear equations is obtained by multiplying all the transformation matrices in Eq. (4) in sequence. The second and third rows are used because the intersection of the imaging plane with the wire along the x-direction, $x_R$, is not known. Two equations per identified wire are thus determined. All matrices are known except the frame-to-device matrix, which has eight unknown parameters. By acquiring a number of ultrasound images of the wires from different orientations, a sufficient number of equations can be defined to solve for the unknown parameters. More equations than unknowns are determined, which means that the problem is overspecified. It can be solved using numerical methods for optimally solving sets of nonlinear equations, such as the Levenberg-Marquardt algorithm. The nonlinearities arise from the trigonometric functions in the transformation matrices.

The resulting nonlinear equations can be solved directly. However a different approach relies on geometric identities to solve the problem linearly to a certain point, and then treats the nonlinearities separately. The advantage of this approach is that it gives greater control over the solution (rather than letting an optimizer find an "optimal" solution).

Figure 4:
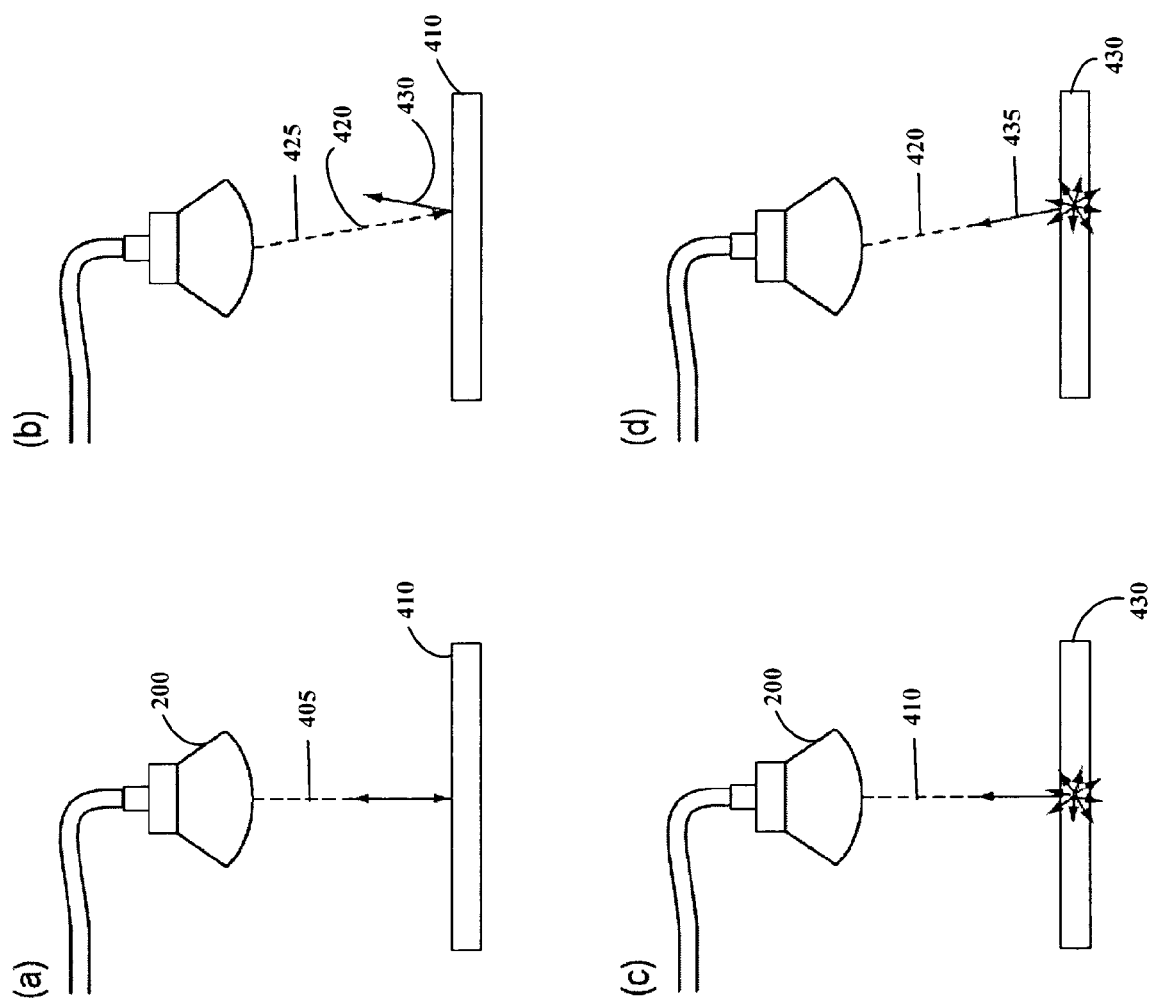
FIGS. 4A-4D are schematic illustrations of various reflection angles from a hand-held imaging probe according to an embodiment of the invention.

Because wires are primarily visible under ultrasound through specular (mirrored) reflection, using wires as the embedded elements within the phantom requires the images to be acquired from near-normal incidence. Referring to FIG. 4(a), specular reflection refers to the high echoes received from the sound waves 405 emitted by ultrasound device 200 upon contact with the wire 410. As shown in FIG. 4(b), however, the angle of incidence 420 of an ultrasonic beam 425 that is not normal to the wire 410 is greater than zero, and therefore the echo 430 is not detected by the ultrasound device. As a result, the image does not contain a representation of the wire 410. To compensate, imaging from multiple sides ("side windows") of the phantom is necessary to obtain sufficient independent images and to assure the images contain representations of the wires, increasing the complexity of the phantom (e.g., incorporation of one or more side windows) and the amount of time required for calibration.

Referring to FIGS. 4(c) and 4(d), in one embodiment of the invention the wires 410 are replaced with elongated members that, because of their shape, size, composition, and/or surface features detectably reflect acoustic signals (e.g., ultrasound signals having a wavelength of about 0.5 mm) regardless of incidence angle of the signal with respect to the members. For example, cylindrical rods 430 may be placed within the body of the phantom. Because the ultrasound signals are reflected by the cylindrical rods 430 in a diffuse manner (rather than the specular reflections characteristic of wires), the rods 430 embedded within the phantom can be seen by distinguishing the diffuse reflection signals originating from the rod compared to signals originating from its surroundings regardless of the angle at which the ultrasound device is targeted at the phantom. Thus, side windows can be eliminated from the phantom, and the number of images required as well as the amount of time required to calibrate the device is reduced. As illustrated in FIGS. 4(c) and 4(d), the reflection of rod 430 can be detected from any viewing angle.

Although described herein as cylindrical rods having a diameter of at least 3 mm, any elongated member having a shape such that cross-sectional images of the members are concentric regardless of the sectional angle, and having sufficient thickness to produce a detectable reflection from any angle cutting through the member, are suitable. As such, the elongated member can be elliptical or cylindrical, or have any number of sides, so long as the above condition is met and the center-point can be identified.

Figure 5B:
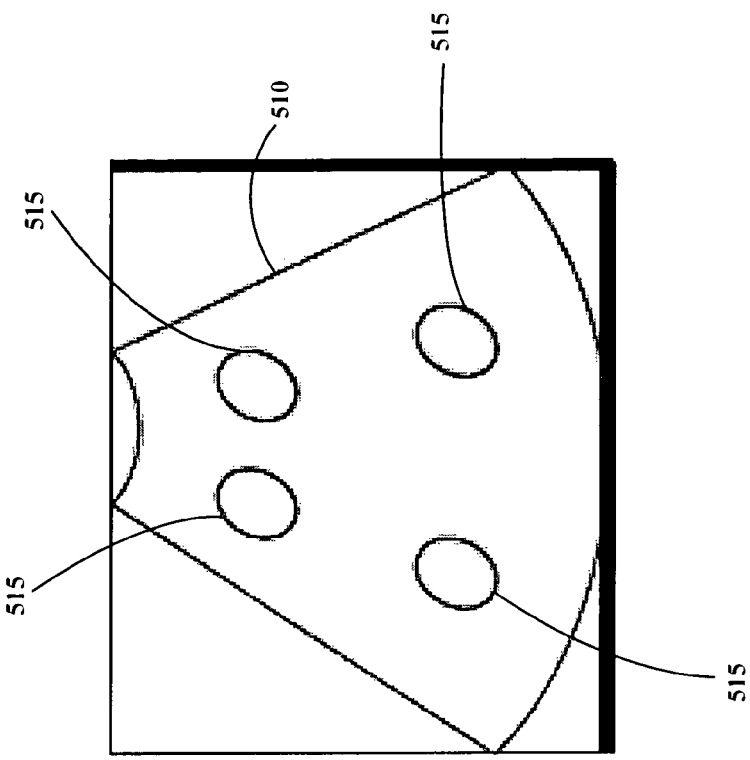
FIGS. 5A and 5B are a perspective view and cross-sectional view, respectively, of a calibration apparatus according to an embodiment of the invention.
Figure 5A:
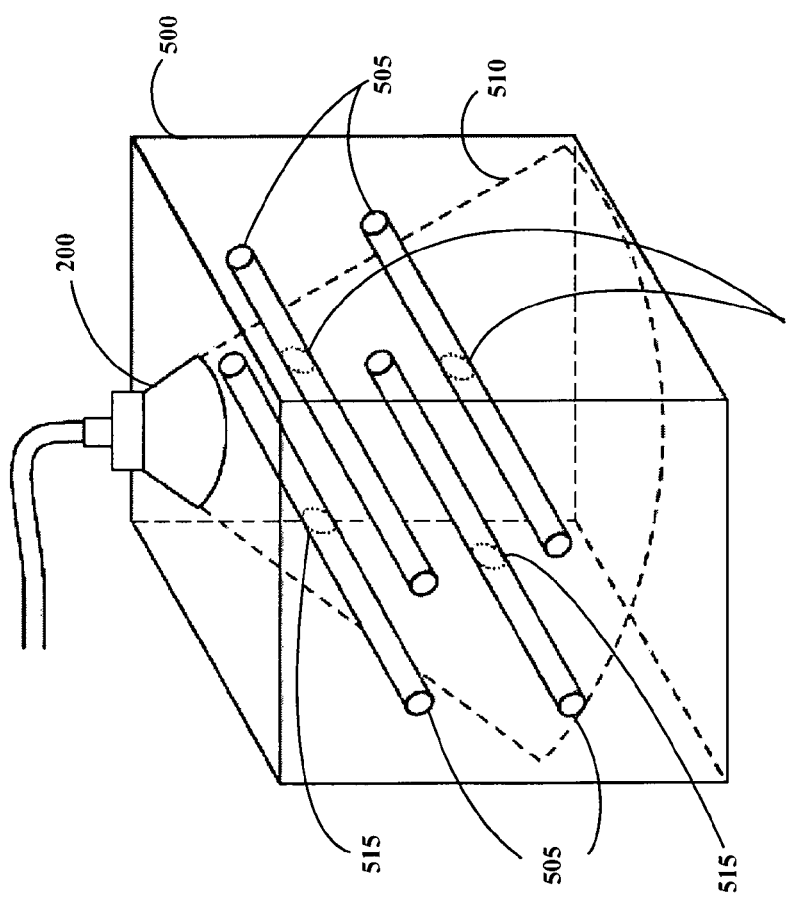

Referring to FIGS. 5A and 5B, multiple view directions may be used to calibrate an imaging device using a phantom.

FIG. 5A illustrates one possible embodiment of a phantom 500 including one or more elongated rods described above as it is used to calibrate an imaging device 200. The imaging device 200 is introduced to the phantom 500 by placing it in, on, or near the phantom such that the rods 505 embedded within the phantom 500 are visible in the resulting image 510. In such images 510, the rods 505 appear as ellipses 515. Those skilled in the art will recognize that many methods, manual or automatic, may then be used to determine the centers of the rods 505 using the ellipses 515. One possible method is described in greater detail below.

Figure 6B:
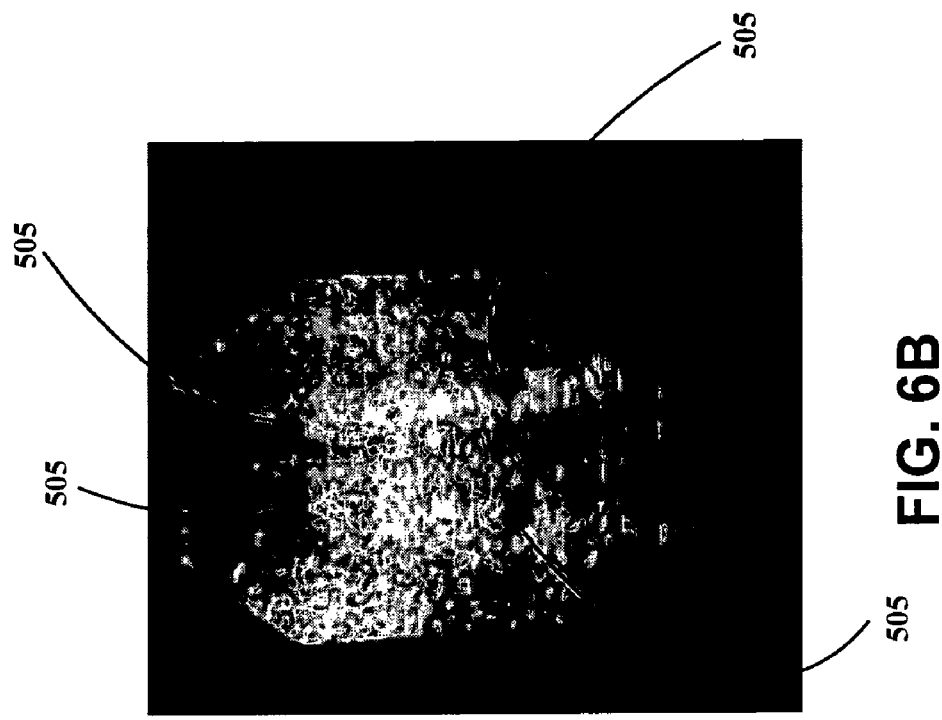
FIGS. 6A and 6B are graphical representations of images of a calibration apparatus according to an embodiment of the invention.
Figure 6A:
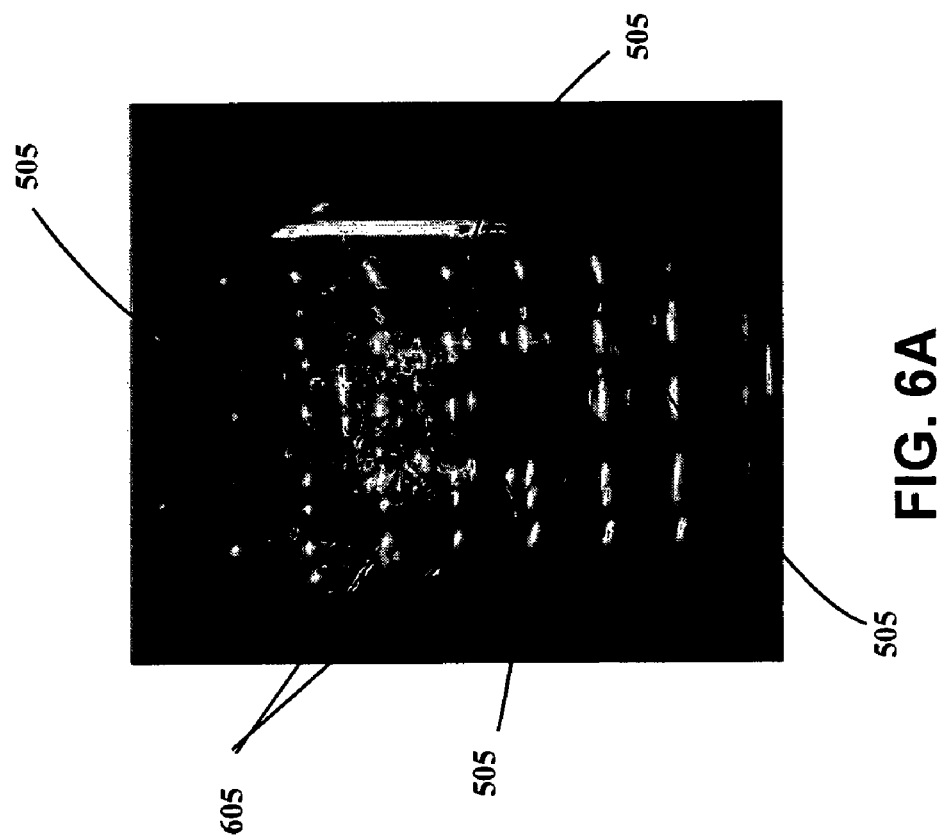

As an illustration, FIG. 6 shows two ultrasound images of the same phantom having both wires and rods embedded within it. The image of FIG. 6(a) is acquired at normal incidence, and thus both rods 505 and wires 605 can be seen. In contrast, FIG. 6(b) illustrates an image acquired at oblique incidence, and the rods 505 remain visible while the wires (noted as 605 in FIG. 6(a)) are no longer imaged by the ultrasound probe. Thus, using a phantom in accordance with the present invention, there are fewer constraints imposed upon the operator with regards to the imaging angles (both in degree and number) during the calibration process.

Figure 7B:
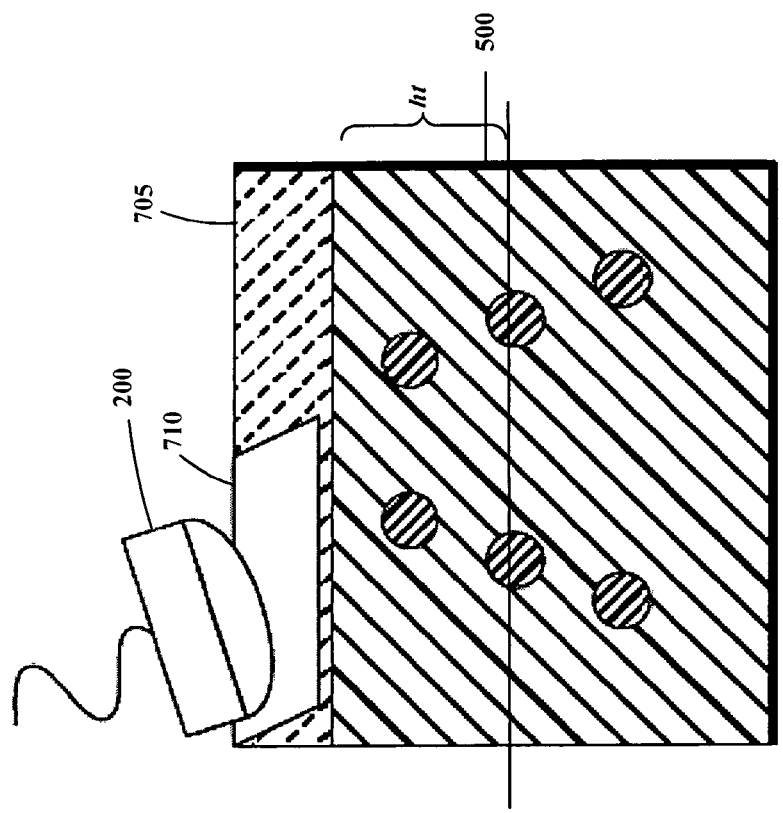
FIGS. 7A and 7B are a top view and cross-sectional view, respectively, of a calibration apparatus according to an embodiment of the invention.
Figure 7A:
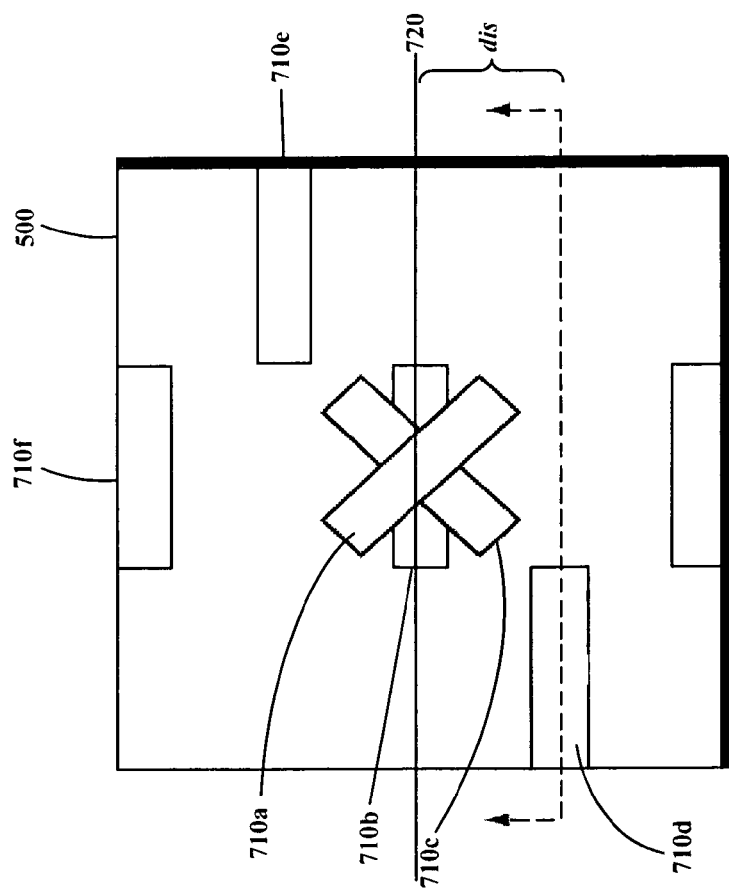

As described above, the calibration phantom is placed at a known location relative to a room coordinate system and images of the phantom are used to calibrate the required transformations. A number of different image "slices" of the calibration phantom are taken, with the probe positioned at different viewing angles or orientations to facilitate calibration. FIGS. 7A and 7B illustrate a preferred set of viewing angles that provide accurate and fast calibration using the phantom 500 in accordance with one embodiment of the invention. To provide a quick reference guide for operators such that they do not have to estimate the correct positioning of the device with respect to the embedded members, a top-plate 705, or "caddy," may be affixed to the top of the phantom 500. The caddy 705 guides the user in identifying the desirable viewing angles by directing the probe's 200 position to an identified target area of the phantom 500. In some cases the target areas can be decals or other graphical indications on the caddy 705, whereas in other embodiments the caddy 705 includes apertures, slots and/or recesses 710 that guide and snugly confine the probe in a particular location and angle. In such instances, the user places the probe 200 in each one or more of the slots 710 and acquires the images. Because multiple images of the phantom 500 are used to calibrate the probe 200, and different angles may provide better images for calibration, a caddy 705 affixed to the top of the phantom 500 that guides the user in choosing a set of predetermined "best" angles improves calibration accuracy and speed.

In one embodiment, the phantom casing can, for example, be made of PLEXIGLASS and the interior can be made of ZERDINE, a material which is manufactured to have the same ultrasonic properties as tissue, such that the speed of sound traveling through the phantom is approximately 1540 m/s. The rods may be made of virtually any material that reflects ultrasound signals. In a particular embodiment the rods are also be made of ZERDINE, however, they have different attenuation characteristics to provide imaging contrast but the same speed-of-sound parameter as the rest of the phantom interior. In one embodiment, the dimensions of the phantom are 20 cm×20 cm×20 cm, and the phantom includes six cylindrical rods of 12 mm diameter each, as shown in FIG. 7B. However, the size and number of rods is not central to the invention, so long as the diameter of the rods is such that the rods remain visible in images acquired at oblique incidence to the rods. Using typical ultrasound devices, a diameter of 3 mm or more is generally sufficient to generate adequate scatters to facilitate the diffusive reflection described above. In some embodiments, the phantom includes an acoustic window on the top having a well-like structure (so that it can be filled with water or some other fluid to improve ultrasonic contact between the phantom and the probe, for example), thus allowing the ultrasound beam to image the interior of the phantom directly. In some embodiments, the walls of the well may be angled to avoid unwanted ultrasonic reflections from the sides of the phantom.

Still referring to FIG. 7A, one embodiment of a phantom 500 includes three slots 710a, 710b and 710c that are aimed normal to the surface of the phantom 500, but which are oriented 120 degrees apart from each other, and may, in some cases, include notches to help fix the probe in any one of the three slots. When received in one of the slots 710, the probe will align to the phantom in any one of the three allowed positions. There may be any number of slots 710, and the degree of offset between slots is not limited in any way as to allow for maximum flexibility in placing the probe 200 in the phantom 500. Two additional slots 710d and 710e are displaced from the center of the phantom 500, but tilted such that they are pointing towards the center of the phantom. In one particular embodiment, the slots 710d and 710e are located a distance dis from the vertical centerline 720 of the phantom 500 and at a height ht above the horizontal centerline 730 of the phantom 500. The preferred degree of tilt is calculated as $\tan^{-1}(ht/dis)$, thus providing a 45 degree tilt when h=d. Two additional slots 710f and 710g are located to the side of the phantom and are parallel the edge, and directed towards the center of the phantom 500. Such alignment angles provide desirable calibration results because they slice through the phantom targets with enough independent image views to solve the required calibration equations. The number of slots, and therefore available positions from which to obtain images may be increased or decreased. Although described herein using tilt angles of 45 degrees, any angle between about 15 and 75 degrees with respect to the horizontal plane of the caddy 705 may be used provided the phantom structures (i.e., the rods) are visible. The positions and angles of the slots may be changed, but those described above give accurate results, fit onto a conveniently sized calibration phantom, and keep the number of images required low for fast and easy calibration of the system.

Figure 8:
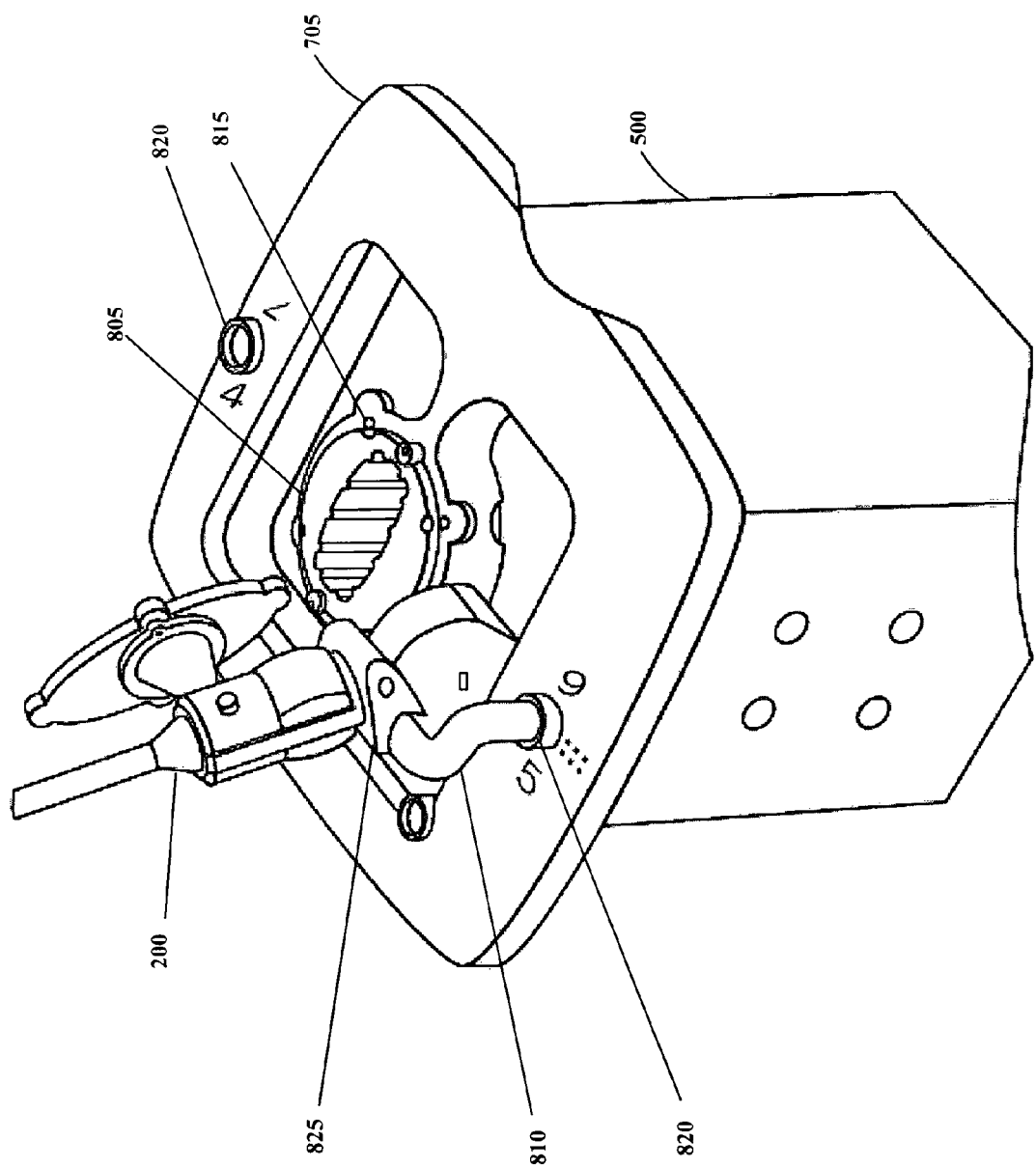
FIG. 8 is a perspective view of a calibration apparatus and hand-held imaging device according to an embodiment of the invention.

FIG. 8 illustrates another embodiment of the invention where the caddy 705 includes a rotating center 805 and one or more removable arms 810. The probe 200 can be inserted in the rotating center 805, and images can be acquired at various angles of rotation (where the axis of rotation runs through the probe 200 to obtain independent scans). The rotating center 805 can have a fixed number of "set points" to ensure that the user can image using the same angles from calibration to calibration. As illustrated, the set points are indexed through the use of magnetic notches 815 in the rotating center 805, but in other embodiments rotation may be indexed by pins, non-magnetic notches, magnets, or other devices that provide allowed set points throughout the rotation of the center 805. In one embodiment, three set points are used, with the second set point being offset 45 degrees clockwise from the first, and the third set point being offset 45 degrees counterclockwise from the first. Instead of, or in addition to the rotating center 805, one or more removable arms 810 may be used to affix the probe 200 to the phantom 500 and rotate the probe 200 about an axis of the arm 810, thus allowing the arm 810 to aim the probe 200 at a number of independent angles. The arm can be placed in various receptacles 820 disposed about the phantom 500 and caddy 705, and the probe 200 affixed thereto using, for example, a removable attachment 825 attached to the probe 200. In some embodiments, a single arm 810 may be used in multiple receptacles 820, and multiple arms 810 may be tailored to hold the probe at varying angles with respect to the phantom 500, the caddy 705 and the rods embedded therein.

Determination of Rod Centers

As described above, once the images of the rods within the phantom are obtained, the centers of the rods are determined in order to properly associate the image coordinate system with the device coordinate system, and thus find the optimal frame-to-device transformation given the rod centers and their known positions in three-dimensional space. One such method for determining the centers of the rods is described below with reference to FIGS. 9, 10 and 11.

One or more ultrasound images containing representations of the cylindrical rods encased in a phantom are obtained. In these images, the rods are represented as black circles or ellipses, depending on the angles from which the images were taken. The x axis corresponds to the width of the image, the y axis to the height of the image, and the origin (0, 0) is defined as the top left corner of the image. An initial guess $(Gx_i, Gy_i)$ of the position of rod i within the ultrasound image and the diameter d of the rods are used to produce the center point $(x_i, y_i)$ of each rod i within the ultrasound image.

Figure 9B:
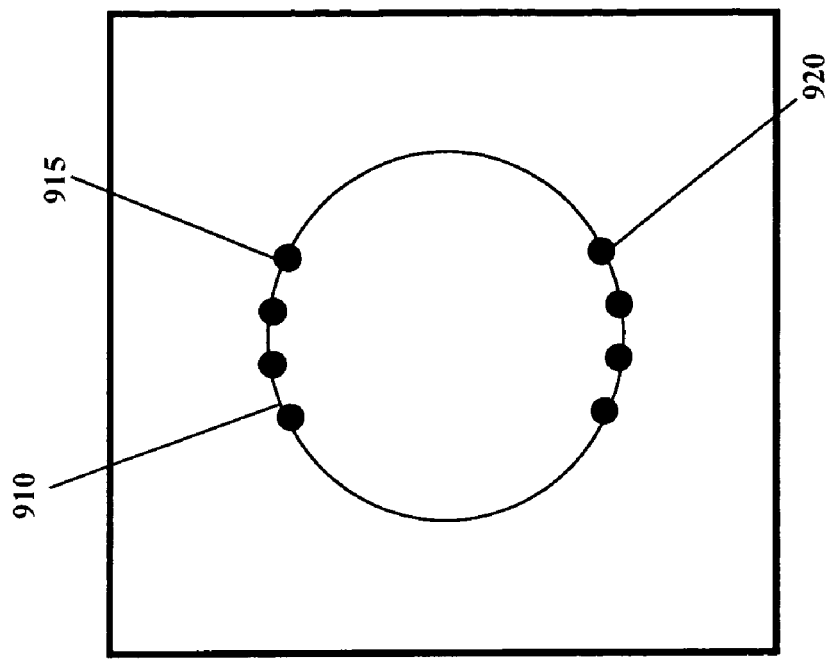
FIGS. 9A and 9B are graphical representations of images of rods within a calibration apparatus according to an embodiment of the invention.
Figure 9A:
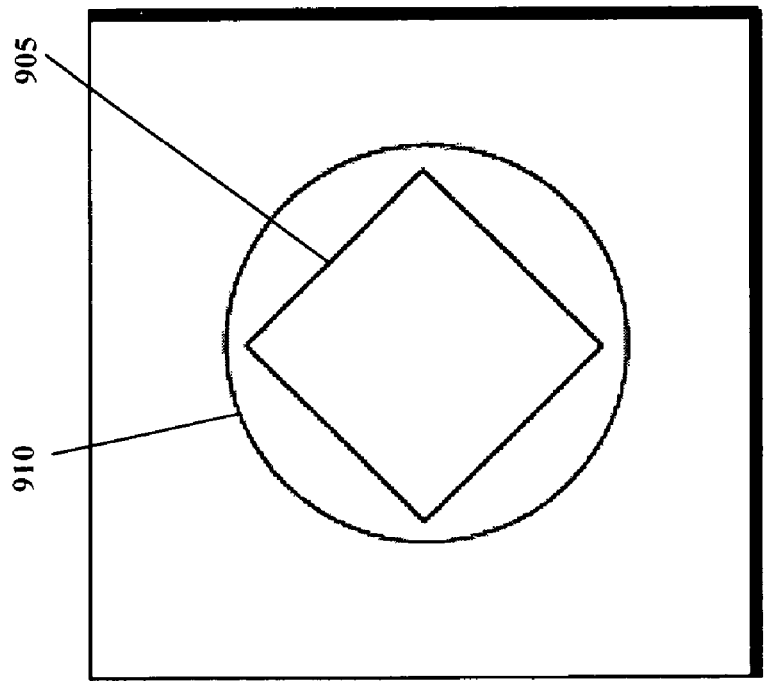

Starting from $(Gx_i, Gy_i)$, the method scans for a rod-like shape by passing over a rotated square 905 as seen in FIG. 9A. Because the representation of the rod within the image is black, the sum of pixel intensities overlapping the rotated square 905 can be calculated, and the location where the rotated square best fits inside a rod 910 is where the sum of pixel intensities is at a minimum. The convolution center $(Cx_i, Cy_i)$ is found for each rod i.

The ultrasound image may be smoothed using a smoothing technique which passes over the input image a 3×3 average kernel, where the middle pixel within the kernel is replaced with the average intensity values of its neighbors.

Starting from $(Cx_i, Cy_i)$, the method finds the top and bottom edges of the rod 910 in which $(Cx_i, Cy_i)$ lies inside as seen in FIG. 9B. This is accomplished by taking the first derivative along the y-axis above and below $(Cx_i, Cy_i)$, as well as for d points to the left and right of $(Cx_i, Cy_i)$. The rod edge is defined as where the largest difference is detected, and a set of top edge points 915 and bottom edge points 920 are determined.

Where a maximum derivative is not detected (for example, if the derivative line lies outside the rod), the pixel location is given as (0, 0). If this happens in only one of the set of edge points, there is a different number of top and bottom detected edge points. To make the number of top edge points equal to the number of bottom edge points, the (0, 0) points are removed and the corresponding points in the opposite set of points is also removed, resulting in two sets of equal size n.

Figure 10B:
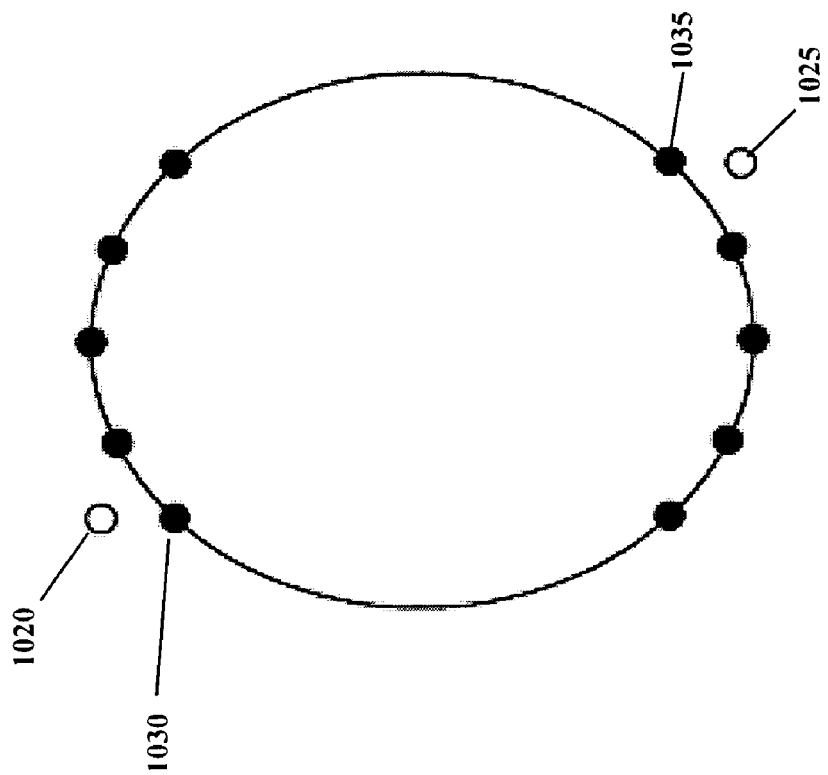
FIGS. 10A and 10B are graphical representations of the edges of rods within a calibration apparatus according to an embodiment of the invention.
Figure 10A:
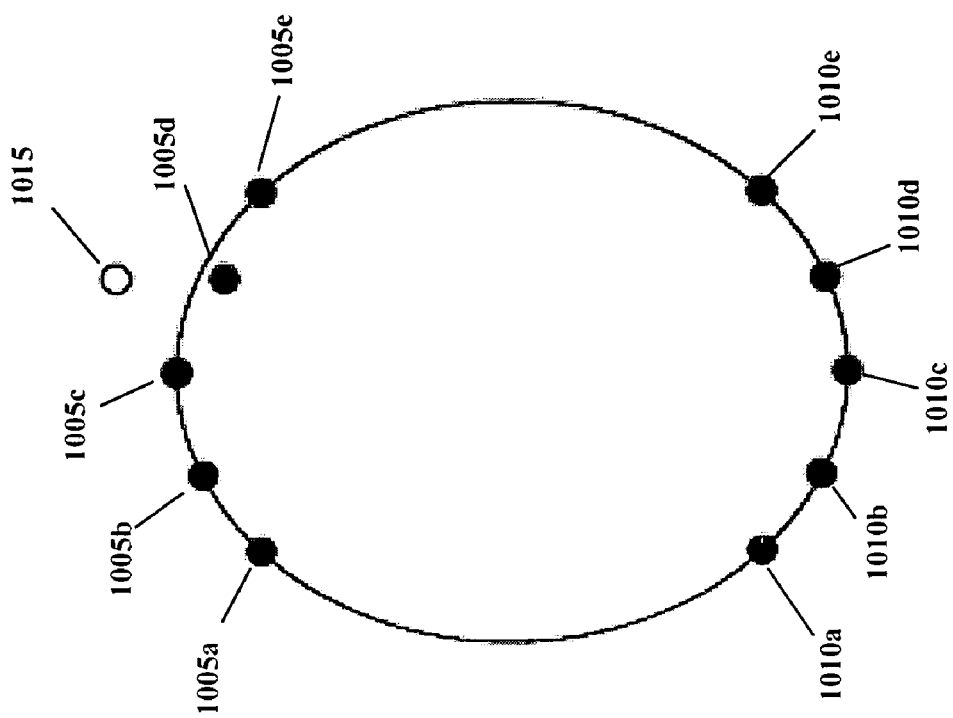

Prior to using the detected edge points in the best-fit ellipse algorithm described below, the distances between opposite pairs of edge points are calculated to minimize the probability that the detected points are image noise (outliers) and to maximize the probability that the geometry of the detected points is a circle or an ellipse. FIGS. 10A and 10B illustrate one method of determining such distances by calculating the distance from each top point 1005a-1005e to each bottom point 1010a-1010e, and calculating an average distance value y for each set of points. If a distance between opposite points is above or below a threshold (the true diameter distance d, for example), the point that is too far from the average value y of the set of points to which it belongs (top set 1005 or bottom set 1010) is replaced with that y value, bringing it closer to the rod edge. Referring to FIG. 10A for example, the distance between top point 1015 and bottom point 1010d is too large and therefore, the top point 1015 will be placed at the average y value for the top set, i.e., at point 1005d. FIG. 10B illustrates another possible example where the first (or last) edge points of a set are not on the edge. For the geometry of the set of points to fit more closely to a circle or an ellipse, these points are forced to have the largest (top edge) or smallest (bottom edge) of a set of y values within the corresponding set of detected points. Thus, 1020 and 1025 in FIG. 10B are replaced with points 1030 and 1035, respectively.

Figure 11B:
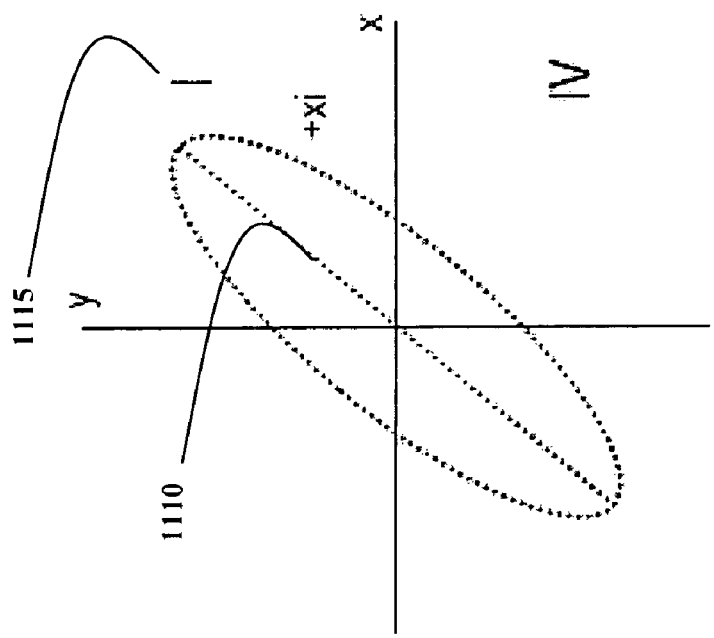
FIGS. 11A and 11B are graphical representations of ellipses formed by the edges of rods within a calibration apparatus according to an embodiment of the invention.
Figure 11A:
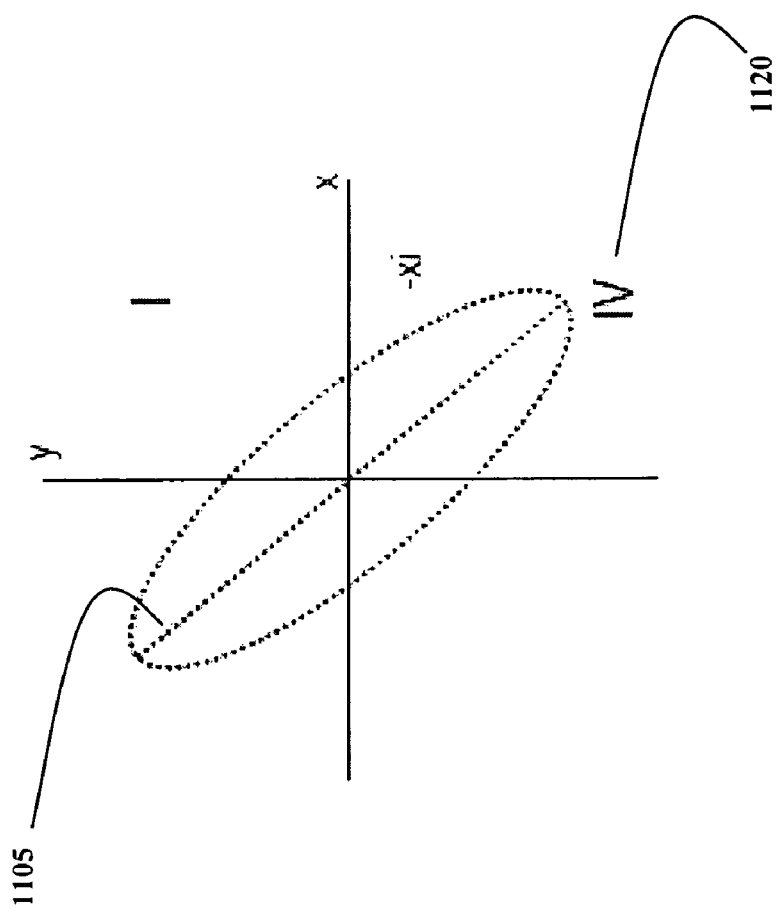

Referring to FIGS. 11A and 11B, using the set of positive points (x, y) determined above for the top and bottom edges of the rod, the ellipse which best fits through those points may be determined. In general, the ellipse function may defined as:

$$x = x_c + p \cdot \cos(\alpha) \cdot \cos(x_i) + q \cdot \sin(\alpha) \cdot \sin(x_i)$$

$$y = y_c - p \cdot \sin(\alpha) \cdot \cos(x_i) + q \cdot \cos(\alpha) \cdot \sin(x_i)$$

and conics in general form may be defined as:

$$f(x, y) = (x \ y \ 1) \begin{pmatrix} a & b & d \\ b & c & e \\ d & e & 1 \end{pmatrix} \begin{pmatrix} x \\ y \\ 1 \end{pmatrix} \tag{6}$$

such that if $s = b^2 - ac > 0$ then $f(x,y)$ is an ellipse. The center of the ellipse is given as:

$$x_c = \frac{be - cd}{ac - b^2} \tag{7}$$

$$y_c = \frac{bd - ae}{ac - b^2} \tag{8}$$

and the axes of the ellipse are given as:

$$p = \sqrt{\frac{\det(A)}{s \cdot a_s}} \tag{9}$$

$$q = \sqrt{\frac{\det(A)}{s \cdot b_s}} \quad \text{where} \tag{10}$$

$$a_s = \frac{1}{2}\left(a + c + \sqrt{(a-c)^2 + 4b^2}\right) \text{ and} \tag{11}$$

$$b_s = \frac{1}{2}\left(a + c - \sqrt{(a-c)^2 + 4b^2}\right). \tag{12}$$

The angle of rotation of the ellipse may then be described by:

$$x_i = \frac{\pi}{2} \text{ where} \tag{13}$$

$$x_i = \frac{a}{2} \tan\left(\frac{2b}{a-c}\right) \text{ if } b \neq c. \tag{14}$$

This approach returns an ellipse defined by its center point $(x_i, y_i)$ for the edge points of rod i, the coordinates of the minor and major axes of the ellipse, and the angle $x_i$ of the ellipse. The angle $x_i$ is the angle between the x-axis and the semi major axes of the ellipse 1105 and 1110. The solution provides two results, one having a positive angle $x_i$ and a second having a negative angle $x_i$. When positive, the ellipse is located in the first quadrant I 1115 of the two-dimensional image coordinate system, and in the fourth quadrant IV 1120 when negative.

The above approach describes one method to find the centers of the ellipses defined by the images of the rods. Other methods can, for example, use segmentation strategies such as level sets or active contours to find the outlines of the rods, and compute the centroid of the outlines to find their respective centers.

Once the rod centers are known, they are used to find the image-to-device transformation using a non-linear optimization technique such as the method described above with respect to the wire-based phantom (i.e., Eq. 4). Another approach to finding the optimal transformation includes the steps of finding three points in one image plane and a fourth point in a second image plane, calculating the scaling, rotation, and translation parameters using the four points from analytical formulas, repeating the previous steps for some number of sets of four points and calculating the transformation that minimizes the maximum (or in some cases average) error within the sets of points using the room and image coordinates.

Transformation of Pixel Data to Room Coordinate System

Once the probe and room calibrations have been performed, the frame-to-device and tracker-to-room transformations are determined. For a given image acquired during a scan of the probe, the pixels can be converted to room coordinates using Eq. (4) above. By assigning three-dimensional coordinates to pixels in each image, the pixel locations can be converted to voxels within a three-dimensional ultrasound dataset expressed in the room coordinates of the simulation or treatment rooms can be generated.

In some embodiments, the ultrasound system may be able to change the image depth, which in turn may change the pixel scaling as well as the definition of the frame coordinate system. The methods described above contemplate calibration at a given depth, which may not be appropriate if the image depth is changed. To address the changing image depth, the number of depths which the user can employ may be limited, and a different probe calibration procedure can be performed for each depth. Another solution contemplates performing the calibration at a single reference depth, and scaling the pixel scaling parameters and frame-to-probe transformations accordingly every time the depth is changed. For example assume matrix $M_0$ (scaling) and matrix $M_1$ (non-scaling part of the frame-to-device transformation) are calibrated at a reference depth $d_{ref}$, whose values are:

$$M_{0,ref} = \begin{bmatrix} s_{x,ref} & 0 & 0 & 0 \\ 0 & s_{y,ref} & 0 & 0 \\ 0 & 0 & 1 & 0 \\ 0 & 0 & 0 & 1 \end{bmatrix}, M_{1,ref} = \begin{bmatrix} R_{ref} & T_{ref} \\ 0 & 1 \end{bmatrix} \quad (15)$$

where $R_{ref}$ is the 3×3 rotation matrix and $T_{ref}$ is the 1×3 translation matrix for $M_1$. Image depths are defined from the probe surface to the bottom of the image. To calculate the matrices $M_0$ and $M_1$ at other depths, the following equations can be used:

$$M_0 = \begin{bmatrix} s_x & 0 & 0 & 0 \\ 0 & s_y & 0 & 0 \\ 0 & 0 & 1 & 0 \\ 0 & 0 & 0 & 1 \end{bmatrix}, M_1 = \begin{bmatrix} R & T \\ 0 & 1 \end{bmatrix} \text{ where} \quad (16)$$

$$s_x = \frac{d+P}{d_{ref}+P_{ref}} s_{x,ref}, \quad (17)$$

$$s_y = \frac{d+P}{d_{ref}+P_{ref}} s_{y,ref}, \quad (18)$$

$$R = R_{ref}, \text{ and} \quad (19)$$

$$T = T_{ref} - R_{ref} \begin{pmatrix} \Delta x \\ \Delta y \\ 0 \end{pmatrix} \text{ where} \quad (20)$$

$$\Delta x = (s_x - s_{x,ref}) \frac{N}{2} \text{ and} \quad (21)$$

$$\Delta y = P \cdot s_y - P_{ref} \cdot s_{y,ref} \quad (22)$$

and N is the number of pixels in the image width. P and $P_{ref}$ refer to the distances between the top of the image and the pixel corresponding to the probe edge in current and reference depth images.

FIG. 12 illustrates one embodiment of the apparatus 1200 for performing the methods described above. The apparatus 1200 includes a register 1210 that receives image data from imaging device 200 (such as the hand-held ultrasound device described above) via a cord or wire 1205, or in some embodiments via wireless communications. The apparatus also includes 1200 a processor 1215 that, based on the images and various coordinate systems (room, tracker, device and frame), uses the methods described above to calibrate the imaging device to the room coordinate system.

In various embodiments the processor 1215 may be provided as either software, hardware, or some combination thereof. For example, the apparatus 1200 may be implemented on one or more server-class computers, such as a PC having a CPU board containing one or more processors such as the Pentium or Celeron family of processors manufactured by Intel Corporation of Santa Clara, Calif., the 680x0 and POWER PC family of processors manufactured by Motorola Corporation of Schaumburg, Ill., the Alpha line of processors manufactured by Compaq Corporation of Houston, Tex., and/or the ATHLON line of processors manufactured by Advanced Micro Devices, Inc., of Sunnyvale, Calif. The processor 1215 may also include a main memory unit for storing programs and/or data relating to the methods described above. The memory may include random access memory (RAM), read only memory (ROM), and/or FLASH memory residing on commonly available hardware such as one or more application specific integrated circuits (ASIC), field programmable gate arrays (FPGA), electrically erasable programmable read-only memories (EEPROM), programmable read-only memories (PROM), programmable logic devices (PLD), or read-only memory devices (ROM). In some embodiments, the programs may be provided using external RAM and/or ROM such as optical disks, magnetic disks, as well as other commonly storage devices.

For embodiments in which the invention is provided as a software program, the program may be written in any one of a number of high level languages such as FORTRAN, PASCAL, JAVA, C, C++, C#, LISP, PERL, BASIC or any suitable programming language. Additionally, the software could be implemented in an assembly language and/or machine language directed to the microprocessor resident on a target device.

It will therefore be seen that the foregoing represents an improved method and supporting apparatuses to calibrating imaging devices. The terms and expressions employed herein are used as terms of description and not of limitation, and there is no intention, in the use of such terms and expressions, of excluding any equivalents of the features shown and described or portions thereof, but it is recognized that various modifications are possible within the scope of the invention claimed. Moreover, although the above-listed text and drawings contain titles headings, it is to be understood that these title and headings do not, and are not intended to limit the present invention, but rather, they serve merely as titles and headings of convenience.

What is claimed is:

1. A method for calibrating an imaging device to a reference coordinate system, the method comprising:
    locating a plurality of elongated members extending substantially though a housing that detectably reflect an acoustic signal regardless of incidence angle or placement of signal source with respect to the members at known positions with respect to a reference coordinate system;
    obtaining a plurality of images taken from different directions directed along the elongated members and comprising cross-sectional representations of the elongated members; and
    calibrating the imaging device to the reference coordinate system based at least in part on the plurality of images by (i) determining the centers of one or more of the members within each representation and (ii) relating the coordinates of the members to the reference coordinate system based on the determined centers.

2. The method of claim 1 wherein the elongated members are rods.

3. The method of claim 2 wherein the rods are cylindrical.

4. The method of claim 2 wherein the rods have a diameter of at least about 3 mm.

5. The method of claim 1 wherein the shape of the elongated member is such that cross-sectional images of the member are concentric regardless of sectional angle.

6. The method of claim 1 wherein the reference coordinate system is a three-dimensional reference coordinate system.

7. The method of claim 6 wherein the three-dimensional reference coordinate system is defined by a series of lasers disposed about a room.

8. The method of claim 6 wherein the three-dimensional reference coordinate system is defined by the physical orientation of a treatment device.

9. The method of claim 6 wherein the three-dimensional reference coordinate system is defined by the physical orientation of an imaging device.

10. The method of claim 1 wherein the plurality of images are two-dimensional ultrasound images.

11. The method of claim 10 wherein the two-dimensional ultrasound images are taken from different angles with respect to the cylindrical rods.

12. The method of claim 11 wherein the angles are orthogonal to the cylindrical rods.

13. The method of claim 11 wherein the angles are oblique to the cylindrical rods.

14. The method of claim 1 wherein the calibration step comprises relating the plurality of images to a coordinate system of the device, and relating the coordinate system of the device to the reference coordinate system.

15. The method of claim 1 further comprising recalibrating the imaging device to the reference coordinate system in response to images taken at an image depth different from that of the obtained plurality of images.

16. A system for calibrating an imaging device to a reference coordinate system, the system comprising:
    a register for receiving a plurality of images imaged from a plurality of locations, the images comprising cross-sectional representations of a plurality of elongated members extending substantially through a housing and having known positions with respect to a reference coordinate system and that detectably reflect an acoustic signal regardless of incidence angle of the signal or placement of the signal source with respect to the members; and
    a processor, responsive to the images, for calibrating the imaging device to the reference coordinate system by (i) determining the centers of one or more of the members within each representation and (ii) relating the coordinates of the members to the reference coordinate system based on the determined centers.

17. The system of claim 16 wherein the elongated members are rods.

18. The system of claim 17 wherein the rods are cylindrical.

19. The system of claim 17 wherein the rods have a diameter of at least about 3 mm.

20. The system of claim 16 wherein the shape of the elongated members is such that cross-sectional images of any one of the member are concentric regardless of sectional angle.

21. The system of claim 16 wherein the reference coordinate system is a three-dimensional reference coordinate system.

22. The system of claim 21 wherein the three-dimensional reference coordinate system is defined by a series of lasers disposed about a room.

23. The system of claim 21 wherein the three-dimensional reference coordinate system is defined by the physical orientation of a treatment device.

24. The system of claim 21 wherein the three-dimensional reference coordinate system is defined by the physical orientation of an imaging device.

25. The system of claim 16 wherein the plurality of images are two-dimensional ultrasound images.

26. The system of claim 16 wherein the processor recalibrates the imaging device to the reference coordinate system in response to a second set of images taken at an image depth different from that of the received plurality of images.

27. An apparatus for calibrating an imaging device to a reference coordinate system, the apparatus comprising:
    a first housing comprising a plurality of elongated members disposed at fixed positions within and extending substantially through the first housing, the fixed positions being registerable to a reference coordinate system and wherein the elongated members detectably reflect an acoustic signal from which the centers of the elongated members may be determined, regardless of incidence angle or placement of the signal source with respect to the members; and
    a second housing displaced upon the first housing, the second housing comprising a plurality of target areas disposed about the second housing for placement of an imaging device such that images taken by the imaging device from arbitrary positions, when placed at the target areas, comprise representations of the elongated members within the first housing.

28. The apparatus of claim 27 wherein the elongated members are rods.

29. The apparatus of claim 28 wherein the rods are cylindrical.

30. The apparatus of claim 28 wherein the rods have a diameter of at least about 3 mm.

31. The apparatus of claim 27 wherein the shape of the elongated members is such that cross-sectional images of any one of the members are concentric regardless of sectional angle.

32. The apparatus of claim 27 wherein the target areas comprise one or more of apertures, slots, and recesses.

33. The apparatus of claim 32 wherein the target areas comprise recesses, and an imaging device is received in close-fitting relation to one or more of the recesses.

34. The apparatus of claim 32 wherein the target areas comprise recesses, and the imaging device is repositionable in more than one orientation within the recess.

35. The apparatus of claim 34 wherein the position of the imaging device is indexable.

36. The apparatus of claim 34 wherein the imaging device is rotatable about an axis passing through the imaging device.

37. The apparatus of claim 34 wherein the imaging device is rotatable about an axis external to the imaging device.

38. The apparatus of claim 27 further comprising one or more support arms temporarily mated to the second housing.

39. The apparatus of claim 38 further comprising one or more openings displaced about the second housing for receiving one of the one or more support arms.

40. The apparatus of claim 38 wherein the imaging device is temporarily mated to the support arm.

41. The apparatus of claim 27 wherein the first housing and second housing are integral.

42. A method for calibrating an imaging device to a reference coordinate system, the method comprising:
   locating, at known positions with respect to a reference coordinate system, one or more objects that diffusely reflect an acoustic signal from an imaging device;
   applying an acoustic signal to the objects without regard to incidence angle or placement of the signal source with respect to the objects to obtain a plurality of images thereof based on diffuse reflection of the signal by the objects; and
   calibrating the imaging device to the reference coordinate system based at least in part on the plurality of images by (i) determining the centers of one or more of the objects within each representation and (ii) relating the coordinates of the objects to the reference coordinate system based on the determined centers.

43. The method of claim 42 wherein the imaging device is an ultrasound probe.

44. The method of claim 42 wherein the reference coordinate system is a three-dimensional reference coordinate system.

45. The method of claim 44 wherein the three-dimensional reference coordinate system is defined by the physical orientation of a treatment device.

46. The method of claim 44 wherein the three-dimensional reference coordinate system is defined by the physical orientation of an imaging device.

* * * * *